United States Patent
Rubin et al.

(10) Patent No.: US 12,178,479 B2
(45) Date of Patent: Dec. 31, 2024

(54) ROD REDUCER ASSEMBLY

(71) Applicant: K2M, Inc., Leesburg, VA (US)

(72) Inventors: Joshua David Rubin, Reston, VA (US); Geneva Goldwood, Tacoma, WA (US); Daniel Genovese, Great Falls, VA (US); Olivia Angus, Pleasanton, CA (US); Robert J. Tokash, Stephens City, VA (US); Ashok Biyani, Sylvania, OH (US); Peter Bono, Bingham Farms, MO (US); Anthony Cucchi, Bloomfield Hills, MI (US); Kornelis Poelstra, Los Gatos, CA (US); Michael Selby, North Adelaide (AU); Robert Kuru, Gateshead (AU)

(73) Assignee: K2M, Inc., Leesburg, VA (US)

( * ) Notice: Subject to any disclaimer, the term of this patent is extended or adjusted under 35 U.S.C. 154(b) by 958 days.

(21) Appl. No.: 17/022,579

(22) Filed: Sep. 16, 2020

(65) Prior Publication Data
US 2021/0068875 A1   Mar. 11, 2021

Related U.S. Application Data

(62) Division of application No. 15/850,169, filed on Dec. 21, 2017, now Pat. No. 10,779,866.
(Continued)

(51) Int. Cl.
*A61B 17/70* (2006.01)
*A61B 17/00* (2006.01)
(Continued)

(52) U.S. Cl.
CPC ...... *A61B 17/7086* (2013.01); *A61B 17/7032* (2013.01); *A61B 17/708* (2013.01);
(Continued)

(58) Field of Classification Search
CPC ........... A61B 17/7077; A61B 17/7083; A61B 17/7085–7086
See application file for complete search history.

(56) References Cited

U.S. PATENT DOCUMENTS

| | | |
|---|---|---|
| 45,338 A | 12/1864 | Nowlan |
| 45,676 A | 12/1864 | Rayner |

(Continued)

FOREIGN PATENT DOCUMENTS

| | | |
|---|---|---|
| AU | 2011200991 B2 | 8/2011 |
| WO | 04096080 A2 | 11/2004 |

(Continued)

OTHER PUBLICATIONS

European Search Report issued in European Appln. No. 17210841.7 dated May 30, 2018.

*Primary Examiner* — Nicholas J Plionis
(74) *Attorney, Agent, or Firm* — Lerner David LLP

(57) ABSTRACT

A rod reducer assembly is provided and is selectively mountable to a pedicle screw assembly. The pedicle screw assembly includes a pedicle screw housing that defines a rod-receiving recess. The pedicle screw assembly includes an extension assembly that is coupled to the pedicle screw housing by a frangible member. The rod reducer is configured to reduce a spinal rod into the rod-receiving recess of the pedicle screw assembly. The rod reducer assembly may include a derotation sleeve configured to inhibit the frangible member from breaking while manipulating a spinal bone.

17 Claims, 26 Drawing Sheets

Related U.S. Application Data

(60) Provisional application No. 62/440,143, filed on Dec. 29, 2016.

(51) Int. Cl.
*A61B 17/88* (2006.01)
*A61B 90/00* (2016.01)

(52) U.S. Cl.
CPC ...... *A61B 17/7091* (2013.01); *A61B 17/8875* (2013.01); *A61B 2017/00367* (2013.01); *A61B 2017/00473* (2013.01); *A61B 17/8891* (2013.01); *A61B 2090/031* (2016.02); *A61B 2090/037* (2016.02)

(56) References Cited

U.S. PATENT DOCUMENTS

| | | |
|---|---|---|
| 1,920,821 A | 8/1933 | Wassenaar |
| 3,244,170 A | 4/1966 | McElvenny |
| 4,263,899 A | 4/1981 | Burgin |
| 5,167,662 A | 12/1992 | Hayes et al. |
| 5,529,571 A | 6/1996 | Daniel |
| 5,672,175 A | 9/1997 | Martin |
| 5,685,826 A | 11/1997 | Bonutti |
| 5,704,937 A | 1/1998 | Martin |
| 5,720,751 A | 2/1998 | Jackson |
| 5,810,878 A | 9/1998 | Burel et al. |
| 5,910,141 A | 6/1999 | Morrison et al. |
| 5,944,658 A | 8/1999 | Koros et al. |
| 6,036,692 A | 3/2000 | Burel et al. |
| 6,112,623 A | 9/2000 | Bigand et al. |
| 6,123,707 A | 9/2000 | Wagner |
| 6,183,472 B1 | 2/2001 | Lutz |
| 6,200,322 B1 | 3/2001 | Branch et al. |
| 6,616,605 B2 | 9/2003 | Wright et al. |
| 6,648,888 B1 | 11/2003 | Shluzas |
| 6,660,006 B2 | 12/2003 | Markworth et al. |
| 6,726,692 B2 | 4/2004 | Bette |
| 6,746,449 B2 | 6/2004 | Jones et al. |
| 6,790,208 B2 | 9/2004 | Oribe et al. |
| 6,849,064 B2 | 2/2005 | Hamada |
| 6,929,606 B2 | 8/2005 | Ritland |
| 6,957,758 B2 | 10/2005 | Aranyi |
| 7,011,660 B2 | 3/2006 | Sherman et al. |
| 7,083,621 B2 | 8/2006 | Shaolian et al. |
| 7,160,300 B2 | 1/2007 | Jackson |
| 7,179,261 B2 | 2/2007 | Sicvol et al. |
| 7,188,626 B2 | 3/2007 | Foley et al. |
| 7,250,052 B2 | 7/2007 | Landry et al. |
| 7,252,673 B2 | 8/2007 | Lim |
| 7,278,995 B2 | 10/2007 | Nichols et al. |
| 7,306,603 B2 | 12/2007 | Boehm, Jr. et al. |
| 7,371,239 B2 | 5/2008 | Dec et al. |
| 7,462,182 B2 | 12/2008 | Lim |
| 7,465,306 B2 | 12/2008 | Pond, Jr. et al. |
| 7,470,279 B2 | 12/2008 | Jackson |
| 7,473,267 B2 | 1/2009 | Nguyen et al. |
| 7,476,240 B2 | 1/2009 | Raymond et al. |
| 7,481,813 B1 | 1/2009 | Purcell |
| 7,491,207 B2 | 2/2009 | Keyer et al. |
| 7,491,208 B2 | 2/2009 | Pond, Jr. et al. |
| 7,491,218 B2 | 2/2009 | Landry et al. |
| 7,497,869 B2 | 3/2009 | Justis |
| 7,527,638 B2 | 5/2009 | Anderson et al. |
| 7,563,264 B2 | 7/2009 | Landry et al. |
| 7,572,281 B2 | 8/2009 | Runco et al. |
| 7,575,581 B2 | 8/2009 | Lovell |
| 7,591,836 B2 | 9/2009 | Dick et al. |
| 7,608,081 B2 | 10/2009 | Abdelgany |
| 7,611,517 B2 | 11/2009 | Lim |
| 7,618,440 B2 | 11/2009 | Gray et al. |
| 7,618,444 B2 | 11/2009 | Shluzas |
| 7,625,376 B2 | 12/2009 | Brumfield et al. |
| 7,625,379 B2 | 12/2009 | Puno et al. |
| 7,651,502 B2 | 1/2010 | Jackson |
| 7,655,008 B2 | 2/2010 | Lenke et al. |
| 7,666,188 B2 | 2/2010 | Anderson et al. |
| 7,666,189 B2 | 2/2010 | Gerber et al. |
| 7,691,132 B2 | 4/2010 | Landry et al. |
| 7,708,763 B2 | 5/2010 | Selover et al. |
| 7,722,617 B2 | 5/2010 | Young et al. |
| 7,744,598 B2 | 6/2010 | Brumfield et al. |
| 7,744,629 B2 | 6/2010 | Hestad et al. |
| 7,749,233 B2 | 7/2010 | Farr et al. |
| 7,776,040 B2 | 8/2010 | Markworth et al. |
| 7,794,464 B2 | 9/2010 | Bridwell et al. |
| 7,799,031 B2 | 9/2010 | Miller et al. |
| 7,811,288 B2 | 10/2010 | Jones et al. |
| 7,854,751 B2 | 12/2010 | Sicvol et al. |
| 7,862,587 B2 | 1/2011 | Jackson |
| 7,887,539 B2 | 2/2011 | Dunbar, Jr. et al. |
| 7,887,541 B2 | 2/2011 | Runco et al. |
| 7,909,830 B2 | 3/2011 | Frigg et al. |
| 7,909,835 B2 | 3/2011 | Oribe et al. |
| 7,914,558 B2 | 3/2011 | Landry et al. |
| 7,918,857 B2 | 4/2011 | Dziedzic et al. |
| 7,918,858 B2 | 4/2011 | Stad et al. |
| 7,922,724 B2 | 4/2011 | Lim |
| 7,922,725 B2 | 4/2011 | Darst Rice et al. |
| 7,922,749 B2 | 4/2011 | Dewey |
| 7,927,334 B2 | 4/2011 | Miller et al. |
| 7,927,360 B2 | 4/2011 | Pond, Jr. et al. |
| 7,931,654 B2 | 4/2011 | Jones et al. |
| 7,931,673 B2 | 4/2011 | Hestad et al. |
| 7,931,677 B2 | 4/2011 | Abdelgany |
| 7,946,982 B2 | 5/2011 | Hamada |
| 7,947,045 B2 | 5/2011 | Hestad et al. |
| 7,951,168 B2 | 5/2011 | Chao et al. |
| 7,951,175 B2 | 5/2011 | Chao et al. |
| 7,955,355 B2 | 6/2011 | Chin |
| 7,981,115 B2 | 7/2011 | Justis et al. |
| 7,985,242 B2 | 7/2011 | Forton et al. |
| 7,988,694 B2 | 8/2011 | Barrus et al. |
| 8,002,798 B2 | 8/2011 | Chin et al. |
| 8,007,516 B2 | 8/2011 | Chao et al. |
| 8,016,832 B2 | 9/2011 | Vonwiller et al. |
| 8,034,084 B2 | 10/2011 | Landry et al. |
| 8,038,699 B2 | 10/2011 | Cohen et al. |
| 8,048,129 B2 | 11/2011 | Forton et al. |
| 8,062,304 B2 | 11/2011 | Blain et al. |
| 8,066,739 B2 | 11/2011 | Jackson |
| 8,075,591 B2 | 12/2011 | Ludwig et al. |
| 8,075,592 B2 | 12/2011 | Landry et al. |
| 8,096,996 B2 | 1/2012 | Gutierrez et al. |
| 8,100,915 B2 | 1/2012 | Jackson |
| 8,105,329 B2 | 1/2012 | Brumfield et al. |
| 8,105,361 B2 | 1/2012 | Anderson et al. |
| 8,142,436 B2 | 3/2012 | Kirschman |
| 8,147,524 B2 | 4/2012 | Piza Vallespir |
| 8,152,810 B2 | 4/2012 | Jackson |
| 8,162,948 B2 | 4/2012 | Jackson |
| 8,162,952 B2 | 4/2012 | Cohen et al. |
| 8,172,847 B2 | 5/2012 | Dziedzic et al. |
| 8,192,438 B2 | 6/2012 | Garamszegi |
| 8,192,440 B2 | 6/2012 | Jones et al. |
| 8,202,304 B2 | 6/2012 | Boehm, Jr. et al. |
| 8,206,395 B2 | 6/2012 | McLean et al. |
| 8,211,110 B1 | 7/2012 | Corin et al. |
| 8,221,426 B2 | 7/2012 | Justis et al. |
| 8,221,474 B2 | 7/2012 | Bridwell et al. |
| 8,230,863 B2 | 7/2012 | Ravikumar et al. |
| 8,235,997 B2 | 8/2012 | Hoffman et al. |
| 8,246,659 B2 | 8/2012 | Vonwiller et al. |
| 8,273,089 B2 | 9/2012 | Jackson |
| 8,277,453 B2 | 10/2012 | Kave et al. |
| 8,277,491 B2 | 10/2012 | Selover et al. |
| 8,287,546 B2 | 10/2012 | King et al. |
| 8,298,138 B2 | 10/2012 | Gorek et al. |
| 8,303,595 B2 | 11/2012 | Jones |
| 8,308,729 B2 | 11/2012 | Nunley et al. |
| 8,308,774 B2 | 11/2012 | Hoffman et al. |
| 8,333,770 B2 | 12/2012 | Hua |
| 8,377,067 B2 | 2/2013 | Jackson |

(56) References Cited

U.S. PATENT DOCUMENTS

| | | |
|---|---|---|
| 8,382,802 B2 | 2/2013 | Boehm, Jr. et al. |
| 8,388,659 B1 | 3/2013 | Lab et al. |
| 8,394,108 B2 | 3/2013 | McLean et al. |
| 8,394,109 B2 | 3/2013 | Hutton et al. |
| 8,398,644 B2 | 3/2013 | Kirschman |
| 8,414,588 B2 | 4/2013 | Stad et al. |
| 8,439,922 B1 | 5/2013 | Arnold et al. |
| 8,439,924 B1 | 5/2013 | McBride et al. |
| 8,454,664 B2 | 6/2013 | McLean |
| 8,469,960 B2 | 6/2013 | Hutton et al. |
| 8,496,685 B2 | 7/2013 | Landry et al. |
| 8,512,383 B2 | 8/2013 | McLean |
| 8,518,082 B2 | 8/2013 | Sicvol et al. |
| 8,523,916 B2 | 9/2013 | Anderson et al. |
| 8,545,505 B2 | 10/2013 | Sandstrom et al. |
| 8,579,942 B2 | 11/2013 | Boehm, Jr. et al. |
| 8,603,145 B2 | 12/2013 | Forton et al. |
| 8,608,780 B2 | 12/2013 | Forton et al. |
| 8,617,210 B2 | 12/2013 | Sicvol et al. |
| 8,632,572 B2 | 1/2014 | Darst Rice et al. |
| 8,636,743 B2 | 1/2014 | Jones et al. |
| 8,647,347 B2 | 2/2014 | Runco et al. |
| 8,685,063 B2 | 4/2014 | Chin |
| 8,690,879 B2 | 4/2014 | Kirschman |
| 8,702,713 B2 | 4/2014 | Nayet et al. |
| 8,721,692 B2 | 5/2014 | Anderson et al. |
| 8,734,490 B2 | 5/2014 | Anderson et al. |
| 8,764,754 B2 | 7/2014 | Butler et al. |
| 8,764,756 B2 | 7/2014 | Jones |
| 8,764,757 B1 | 7/2014 | Tumialan |
| 8,771,277 B2 | 7/2014 | Zappacosta et al. |
| 8,777,954 B2 | 7/2014 | McLean |
| 8,784,424 B2 | 7/2014 | Tsuang et al. |
| 8,795,283 B2 | 8/2014 | Petit |
| 8,808,296 B2 | 8/2014 | Frigg et al. |
| 8,821,502 B2 | 9/2014 | Gleeson et al. |
| 8,828,005 B2 | 9/2014 | Birkmeyer et al. |
| 8,828,006 B2 | 9/2014 | Semler et al. |
| 8,828,007 B2 | 9/2014 | Stad et al. |
| 8,834,474 B2 | 9/2014 | Jones et al. |
| 8,845,640 B2 | 9/2014 | McLean et al. |
| 8,845,648 B2 | 9/2014 | Guzman et al. |
| 8,845,649 B2 | 9/2014 | Jackson |
| 8,864,767 B2 | 10/2014 | Blain et al. |
| 8,870,879 B2 | 10/2014 | Tsuang et al. |
| 8,870,880 B2 | 10/2014 | Himmelberger et al. |
| 8,870,890 B2 | 10/2014 | Aschmann et al. |
| 8,882,817 B2 | 11/2014 | Jones et al. |
| 8,894,655 B2 | 11/2014 | Fallin et al. |
| 8,894,656 B2 | 11/2014 | Levy et al. |
| 8,894,657 B2 | 11/2014 | Jackson |
| 8,900,237 B2 | 12/2014 | Ramsay et al. |
| 8,900,238 B2 | 12/2014 | Iott et al. |
| 8,900,240 B2 | 12/2014 | White et al. |
| 8,911,442 B2 | 12/2014 | Wing et al. |
| RE45,338 E | 1/2015 | Chin et al. |
| 8,932,210 B2 | 1/2015 | Woods |
| 8,932,296 B2 | 1/2015 | Neary et al. |
| 8,936,606 B2 | 1/2015 | Gleason et al. |
| 8,956,360 B2 | 2/2015 | Boachie-Adjei et al. |
| 8,956,361 B2 | 2/2015 | Davenport et al. |
| 8,956,362 B2 | 2/2015 | Landry et al. |
| 8,992,536 B2 | 3/2015 | Piza Vallespir et al. |
| 9,050,148 B2 | 6/2015 | Jackson |
| 9,055,978 B2 | 6/2015 | Jackson |
| 9,060,825 B2 | 6/2015 | Hutton et al. |
| 9,066,758 B2 | 6/2015 | Justis et al. |
| 9,066,761 B2 | 6/2015 | McBride et al. |
| 9,066,762 B2 | 6/2015 | Jones et al. |
| 9,078,709 B2 | 7/2015 | McBride |
| 9,095,386 B2 | 8/2015 | Butler et al. |
| 9,101,414 B2 | 8/2015 | King et al. |
| 9,101,415 B2 | 8/2015 | Jackson |
| RE45,676 E | 9/2015 | Chin et al. |
| 9,125,703 B2 | 9/2015 | McClintock et al. |
| 9,161,786 B2 | 10/2015 | Anderson et al. |
| 9,173,682 B2 | 11/2015 | Jackson |
| 9,179,926 B2 | 11/2015 | Ludwig et al. |
| 9,179,947 B2 | 11/2015 | Bass |
| 9,198,698 B1 | 12/2015 | Doose et al. |
| 9,452,000 B2 | 9/2016 | Barrus |
| 9,517,099 B2 | 12/2016 | Bess et al. |
| 9,737,351 B2 | 8/2017 | McClintock et al. |
| 9,907,582 B1 | 3/2018 | Olea |
| 2002/0052603 A1 | 5/2002 | Nichols et al. |
| 2003/0199872 A1 | 10/2003 | Markworth et al. |
| 2004/0172022 A1 | 9/2004 | Landry et al. |
| 2004/0230191 A1 | 11/2004 | Frey et al. |
| 2004/0267275 A1 | 12/2004 | Cournoyer et al. |
| 2005/0131422 A1 | 6/2005 | Anderson et al. |
| 2005/0192579 A1 | 9/2005 | Jackson |
| 2005/0245928 A1 | 11/2005 | Colleran et al. |
| 2006/0004380 A1 | 1/2006 | DiDomenico et al. |
| 2006/0025769 A1 | 2/2006 | Dick et al. |
| 2006/0074418 A1 | 4/2006 | Jackson |
| 2006/0111712 A1 | 5/2006 | Jackson |
| 2006/0122597 A1 | 6/2006 | Jones et al. |
| 2006/0184178 A1 | 8/2006 | Jackson |
| 2006/0200132 A1 | 9/2006 | Chao et al. |
| 2006/0247645 A1 | 11/2006 | Wilcox et al. |
| 2006/0247649 A1 | 11/2006 | Rezach et al. |
| 2006/0264934 A1 | 11/2006 | Fallin |
| 2006/0271050 A1 | 11/2006 | Piza Vallespir |
| 2006/0293680 A1 | 12/2006 | Jackson |
| 2007/0055247 A1 | 3/2007 | Jahng |
| 2007/0093817 A1 | 4/2007 | Barrus et al. |
| 2007/0129731 A1 | 6/2007 | Sicvol et al. |
| 2007/0162009 A1 | 7/2007 | Chao et al. |
| 2007/0162010 A1 | 7/2007 | Chao et al. |
| 2007/0213715 A1 | 9/2007 | Bridwell et al. |
| 2007/0213716 A1 | 9/2007 | Lenke et al. |
| 2007/0233079 A1 | 10/2007 | Fallin et al. |
| 2007/0233097 A1 | 10/2007 | Anderson et al. |
| 2007/0270811 A1 | 11/2007 | Dewey |
| 2007/0270867 A1 | 11/2007 | Miller et al. |
| 2007/0282337 A1 | 12/2007 | Garamszegi |
| 2008/0015601 A1 | 1/2008 | Castro et al. |
| 2008/0045970 A1 | 2/2008 | Saidha et al. |
| 2008/0077138 A1 | 3/2008 | Cohen et al. |
| 2008/0077155 A1 | 3/2008 | Diederich et al. |
| 2008/0119849 A1* | 5/2008 | Beardsley ............ A61B 17/708 606/306 |
| 2008/0119862 A1 | 5/2008 | Wicker et al. |
| 2008/0125789 A1 | 5/2008 | Butters et al. |
| 2008/0172062 A1 | 7/2008 | Donahue et al. |
| 2008/0300638 A1 | 12/2008 | Beardsley et al. |
| 2009/0018593 A1 | 1/2009 | Barrus et al. |
| 2009/0062857 A1 | 3/2009 | Ramsay et al. |
| 2009/0082775 A1 | 3/2009 | Altarac et al. |
| 2009/0088764 A1 | 4/2009 | Stad et al. |
| 2009/0138056 A1 | 5/2009 | Anderson et al. |
| 2009/0143828 A1 | 6/2009 | Stad et al. |
| 2009/0149892 A1 | 6/2009 | Stad et al. |
| 2009/0157125 A1 | 6/2009 | Hoffman et al. |
| 2009/0171391 A1 | 7/2009 | Hutton et al. |
| 2009/0228052 A1 | 9/2009 | Beardsley et al. |
| 2009/0228053 A1 | 9/2009 | Kolb et al. |
| 2009/0228055 A1 | 9/2009 | Jackson |
| 2009/0259262 A1 | 10/2009 | Nayet |
| 2009/0281582 A1 | 11/2009 | Villa et al. |
| 2009/0292308 A1 | 11/2009 | Jones et al. |
| 2009/0326586 A1 | 12/2009 | Duarte |
| 2010/0024487 A1 | 2/2010 | Khoo et al. |
| 2010/0030283 A1 | 2/2010 | King et al. |
| 2010/0036443 A1 | 2/2010 | Hutton et al. |
| 2010/0121385 A1 | 5/2010 | Blain et al. |
| 2010/0131016 A1 | 5/2010 | Gerber et al. |
| 2010/0249856 A1 | 9/2010 | Iott et al. |
| 2010/0292742 A1* | 11/2010 | Stad .................. A61B 17/7091 606/279 |
| 2010/0324610 A1 | 12/2010 | Bridwell et al. |
| 2010/0331849 A1 | 12/2010 | Riesinger et al. |
| 2011/0004222 A1 | 1/2011 | Biedermann et al. |
| 2011/0015678 A1 | 1/2011 | Jackson |

(56) References Cited

U.S. PATENT DOCUMENTS

| | | |
|---|---|---|
| 2011/0034962 A1 | 2/2011 | Dunbar, Jr. et al. |
| 2011/0077690 A1 | 3/2011 | Shin et al. |
| 2011/0106082 A1 | 5/2011 | Kave et al. |
| 2011/0118791 A1 | 5/2011 | Nunley et al. |
| 2011/0130793 A1 | 6/2011 | Woolley |
| 2011/0137350 A1 | 6/2011 | Stad et al. |
| 2011/0137358 A1 | 6/2011 | Manninen |
| 2011/0152940 A1 | 6/2011 | Frigg et al. |
| 2011/0172714 A1 | 7/2011 | Boachie-Adjei et al. |
| 2011/0172723 A1 | 7/2011 | Miller et al. |
| 2011/0178560 A1* | 7/2011 | Butler ............... A61B 17/8863 606/86 A |
| 2011/0184469 A1 | 7/2011 | Ballard et al. |
| 2011/0196426 A1 | 8/2011 | Peukert et al. |
| 2011/0208254 A1 | 8/2011 | Villa et al. |
| 2011/0238120 A1 | 9/2011 | Chin |
| 2011/0245881 A1 | 10/2011 | Mitchell |
| 2011/0257690 A1 | 10/2011 | Rezach |
| 2011/0257692 A1 | 10/2011 | Sandstrom et al. |
| 2011/0282390 A1 | 11/2011 | Hua |
| 2011/0282402 A1 | 11/2011 | Chao et al. |
| 2011/0295328 A1 | 12/2011 | Woolley et al. |
| 2011/0313470 A1 | 12/2011 | McLean et al. |
| 2011/0313477 A1 | 12/2011 | McLean et al. |
| 2011/0319938 A1 | 12/2011 | Piza Vallespir et al. |
| 2012/0016424 A1 | 1/2012 | Kave |
| 2012/0022594 A1 | 1/2012 | Walker et al. |
| 2012/0031792 A1 | 2/2012 | Petit |
| 2012/0035668 A1 | 2/2012 | Manninen et al. |
| 2012/0046699 A1 | 2/2012 | Jones et al. |
| 2012/0078308 A1 | 3/2012 | Dziedzic et al. |
| 2012/0083853 A1 | 4/2012 | Boachie-Adjei et al. |
| 2012/0089150 A1 | 4/2012 | Smith |
| 2012/0109208 A1 | 5/2012 | Justis et al. |
| 2012/0116467 A1 | 5/2012 | King et al. |
| 2012/0191137 A1 | 7/2012 | Butters et al. |
| 2012/0191143 A1 | 7/2012 | Nayet et al. |
| 2012/0191144 A1 | 7/2012 | Peultier et al. |
| 2012/0197297 A1 | 8/2012 | Bootwala et al. |
| 2012/0209332 A1 | 8/2012 | Janowski |
| 2012/0239096 A1 | 9/2012 | Gleeson et al. |
| 2012/0239097 A1 | 9/2012 | Garamszegi |
| 2012/0253402 A1 | 10/2012 | McLean |
| 2012/0271365 A1 | 10/2012 | Daubs et al. |
| 2012/0277800 A1 | 11/2012 | Jackson |
| 2012/0277808 A1 | 11/2012 | May |
| 2012/0323279 A1 | 12/2012 | Tsuang et al. |
| 2013/0012999 A1 | 1/2013 | Petit |
| 2013/0018419 A1 | 1/2013 | Rezach et al. |
| 2013/0030445 A1 | 1/2013 | Dauster et al. |
| 2013/0046344 A1 | 2/2013 | Nunley et al. |
| 2013/0046345 A1 | 2/2013 | Jones et al. |
| 2013/0066385 A1 | 3/2013 | Benoist |
| 2013/0066386 A1 | 3/2013 | Biedermann et al. |
| 2013/0079827 A1 | 3/2013 | Neary et al. |
| 2013/0085536 A1 | 4/2013 | Biedermann et al. |
| 2013/0096635 A1 | 4/2013 | Wall et al. |
| 2013/0096637 A1 | 4/2013 | Richelsoph et al. |
| 2013/0103039 A1* | 4/2013 | Hopkins ............ A61B 17/7082 606/104 |
| 2013/0103094 A1 | 4/2013 | Beale et al. |
| 2013/0103095 A1 | 4/2013 | Brumfield et al. |
| 2013/0103096 A1 | 4/2013 | Miller |
| 2013/0110184 A1 | 5/2013 | Wing et al. |
| 2013/0144349 A1 | 6/2013 | Corin |
| 2013/0150898 A1 | 6/2013 | Wong et al. |
| 2013/0165977 A1 | 6/2013 | Biedermann et al. |
| 2013/0172947 A1 | 7/2013 | Greenberg |
| 2013/0184763 A1 | 7/2013 | McClintock et al. |
| 2013/0238037 A1 | 9/2013 | Stad et al. |
| 2013/0245691 A1 | 9/2013 | Hutton et al. |
| 2013/0245692 A1 | 9/2013 | Hayes et al. |
| 2013/0245694 A1 | 9/2013 | Choi et al. |
| 2013/0253598 A1 | 9/2013 | Jackson |
| 2013/0261679 A1 | 10/2013 | McBride et al. |
| 2013/0274754 A1 | 10/2013 | Hutton et al. |
| 2013/0274804 A1 | 10/2013 | Hutton et al. |
| 2013/0289633 A1 | 10/2013 | Gleeson et al. |
| 2013/0296949 A1 | 11/2013 | Sicvol et al. |
| 2013/0304130 A1 | 11/2013 | Jackson |
| 2014/0012321 A1 | 1/2014 | Hutton et al. |
| 2014/0018860 A1 | 1/2014 | Butters et al. |
| 2014/0031828 A1 | 1/2014 | Patel et al. |
| 2014/0039557 A1 | 2/2014 | Stad et al. |
| 2014/0039567 A1 | 2/2014 | Hoefer et al. |
| 2014/0046372 A1 | 2/2014 | Ibrahim et al. |
| 2014/0046388 A1 | 2/2014 | Reichen et al. |
| 2014/0052139 A1 | 2/2014 | Manninen |
| 2014/0052191 A1 | 2/2014 | Manninen |
| 2014/0052197 A1 | 2/2014 | McBride et al. |
| 2014/0074106 A1 | 3/2014 | Shin |
| 2014/0074171 A1 | 3/2014 | Hutton et al. |
| 2014/0100583 A1 | 4/2014 | Butler et al. |
| 2014/0100613 A1 | 4/2014 | Tott et al. |
| 2014/0100617 A1 | 4/2014 | Sandstrom et al. |
| 2014/0100618 A1 | 4/2014 | Kolb et al. |
| 2014/0107707 A1 | 4/2014 | Rovner |
| 2014/0114354 A1 | 4/2014 | May et al. |
| 2014/0128930 A1 | 5/2014 | Meyer et al. |
| 2014/0135854 A1 | 5/2014 | Dec et al. |
| 2014/0135855 A1 | 5/2014 | Jones et al. |
| 2014/0142642 A1 | 5/2014 | Wallenstein et al. |
| 2014/0148865 A1 | 5/2014 | Hennard et al. |
| 2014/0163575 A1 | 6/2014 | Thoren et al. |
| 2014/0163625 A1 | 6/2014 | Meyer et al. |
| 2014/0172019 A1 | 6/2014 | Chin |
| 2014/0172030 A1 | 6/2014 | Harris et al. |
| 2014/0188182 A1 | 7/2014 | Chao et al. |
| 2014/0194939 A1 | 7/2014 | Seelig |
| 2014/0222077 A1 | 8/2014 | Jackson |
| 2014/0222081 A1 | 8/2014 | Kirschman |
| 2014/0222083 A1 | 8/2014 | Anderson et al. |
| 2014/0222090 A1 | 8/2014 | Jackson |
| 2014/0222092 A1 | 8/2014 | Anderson et al. |
| 2014/0249591 A1 | 9/2014 | Peultier et al. |
| 2014/0249592 A1 | 9/2014 | Black et al. |
| 2014/0257312 A1 | 9/2014 | Solitario, Jr. et al. |
| 2014/0257416 A1 | 9/2014 | Meyer et al. |
| 2014/0276895 A1 | 9/2014 | Jackson et al. |
| 2014/0277151 A1* | 9/2014 | Fowler ............... A61B 17/708 606/265 |
| 2014/0277167 A1 | 9/2014 | Hutton et al. |
| 2014/0277168 A1 | 9/2014 | Hutton et al. |
| 2014/0277195 A1 | 9/2014 | McBride |
| 2014/0277196 A1 | 9/2014 | Foley et al. |
| 2014/0277197 A1 | 9/2014 | Brown et al. |
| 2014/0277198 A1 | 9/2014 | Stad |
| 2014/0277200 A1 | 9/2014 | Parker et al. |
| 2014/0277203 A1 | 9/2014 | Atoulikian et al. |
| 2014/0277204 A1 | 9/2014 | Sandhu |
| 2014/0277205 A1 | 9/2014 | Stein et al. |
| 2014/0277206 A1 | 9/2014 | Reitblat et al. |
| 2014/0296862 A1 | 10/2014 | Stad et al. |
| 2014/0316419 A1 | 10/2014 | Perry |
| 2014/0316475 A1 | 10/2014 | Parikh et al. |
| 2014/0316476 A1 | 10/2014 | Michelson |
| 2014/0316477 A1 | 10/2014 | Milz et al. |
| 2014/0336717 A1 | 11/2014 | Predick |
| 2014/0350612 A1 | 11/2014 | Leroux et al. |
| 2014/0350614 A1 | 11/2014 | Frey et al. |
| 2014/0358186 A1 | 12/2014 | Frock et al. |
| 2015/0039035 A1 | 2/2015 | Kruger |
| 2015/0051653 A1 | 2/2015 | Cryder et al. |
| 2015/0057713 A1 | 2/2015 | Iott et al. |
| 2015/0066042 A1 | 3/2015 | Cummins et al. |
| 2015/0066084 A1 | 3/2015 | Petit |
| 2015/0066089 A1 | 3/2015 | Nelson et al. |
| 2015/0080957 A1 | 3/2015 | Jackson |
| 2015/0080962 A1 | 3/2015 | Jackson |
| 2015/0080965 A1 | 3/2015 | Jackson |
| 2015/0080974 A1 | 3/2015 | Jackson |
| 2015/0088210 A1 | 3/2015 | Reitblat et al. |
| 2015/0112397 A1 | 4/2015 | Petit |
| 2015/0142004 A1 | 5/2015 | Gleeson et al. |

(56) References Cited

U.S. PATENT DOCUMENTS

| | | |
|---|---|---|
| 2015/0142060 A1 | 5/2015 | Jackson |
| 2015/0148845 A1 | 5/2015 | Landry et al. |
| 2015/0150606 A1 | 6/2015 | Jackson |
| 2015/0164569 A1 | 6/2015 | Reitblat et al. |
| 2015/0173803 A1 | 6/2015 | Droulout |
| 2015/0182265 A1 | 7/2015 | Biedermann et al. |
| 2015/0238235 A1 | 8/2015 | Tuten |
| 2015/0272631 A1 | 10/2015 | Jackson |
| 2015/0297264 A1 | 10/2015 | King et al. |
| 2015/0297277 A1 | 10/2015 | Jones et al. |
| 2015/0305781 A1 | 10/2015 | Landry et al. |
| 2016/0000478 A1 | 1/2016 | Fischer et al. |
| 2016/0106408 A1 | 4/2016 | Ponmudi et al. |
| 2016/0262807 A1 | 9/2016 | Benson |
| 2016/0345952 A1 | 12/2016 | Kucharzyk et al. |

FOREIGN PATENT DOCUMENTS

| | | |
|---|---|---|
| WO | 05018490 A2 | 3/2005 |
| WO | 05058386 A2 | 6/2005 |
| WO | 05060534 A2 | 7/2005 |
| WO | 05094416 A2 | 10/2005 |
| WO | 06052504 A2 | 5/2006 |
| WO | 07087516 A1 | 8/2007 |
| WO | 10039817 A2 | 4/2010 |
| WO | 2011109507 A2 | 9/2011 |
| WO | 2011159492 A1 | 12/2011 |
| WO | 2013170262 A2 | 11/2013 |
| WO | 2017027694 A1 | 2/2017 |

\* cited by examiner

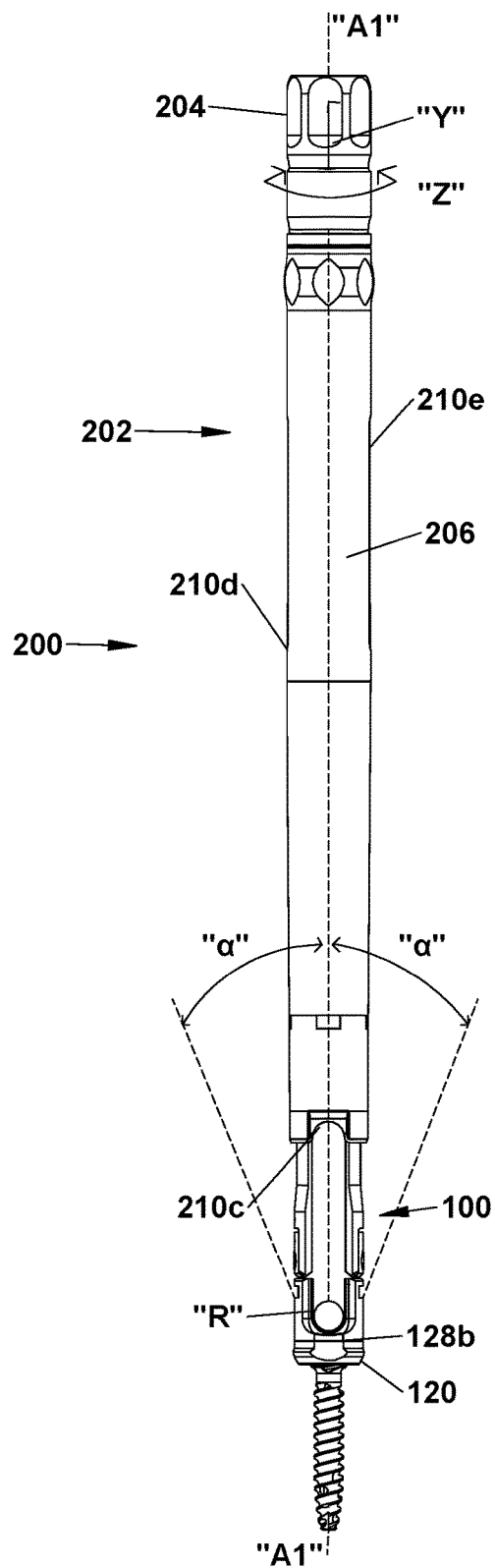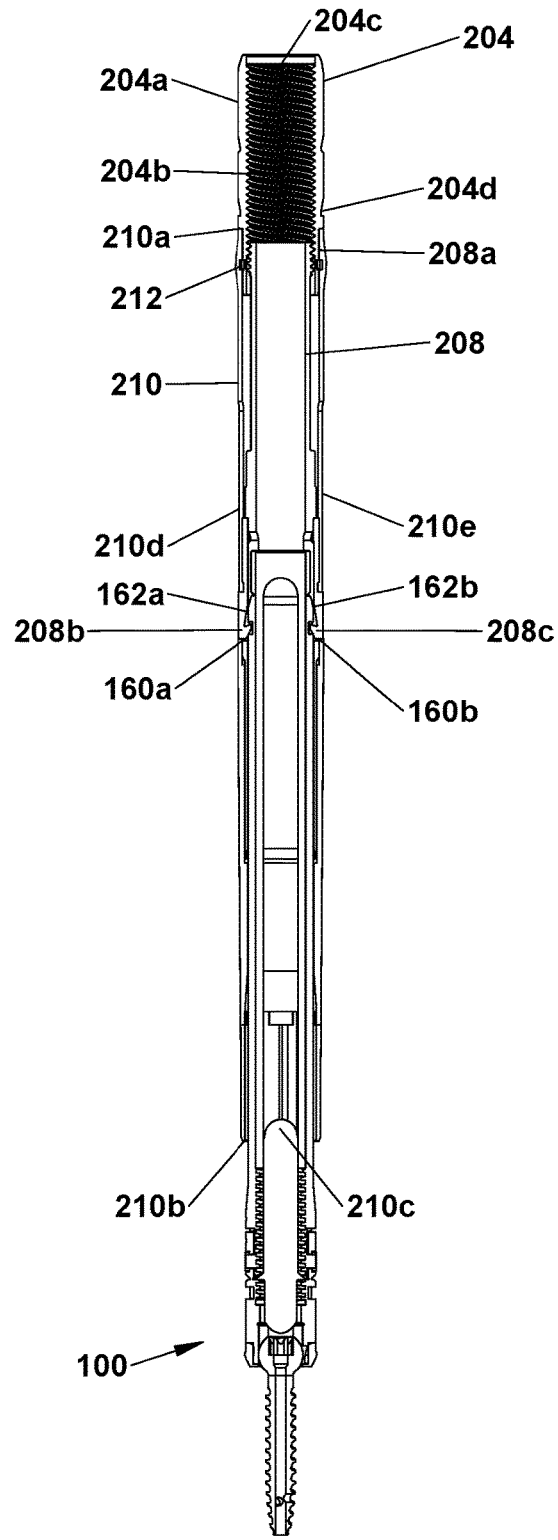
FIG. 3A
FIG. 3B

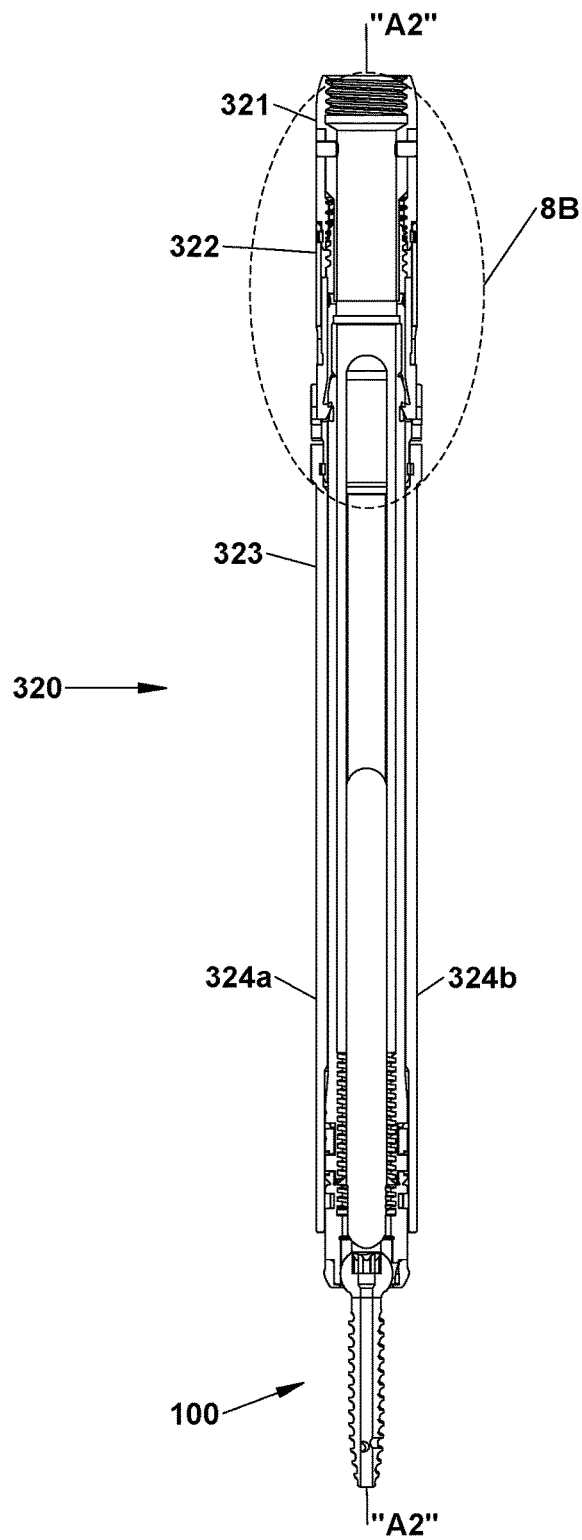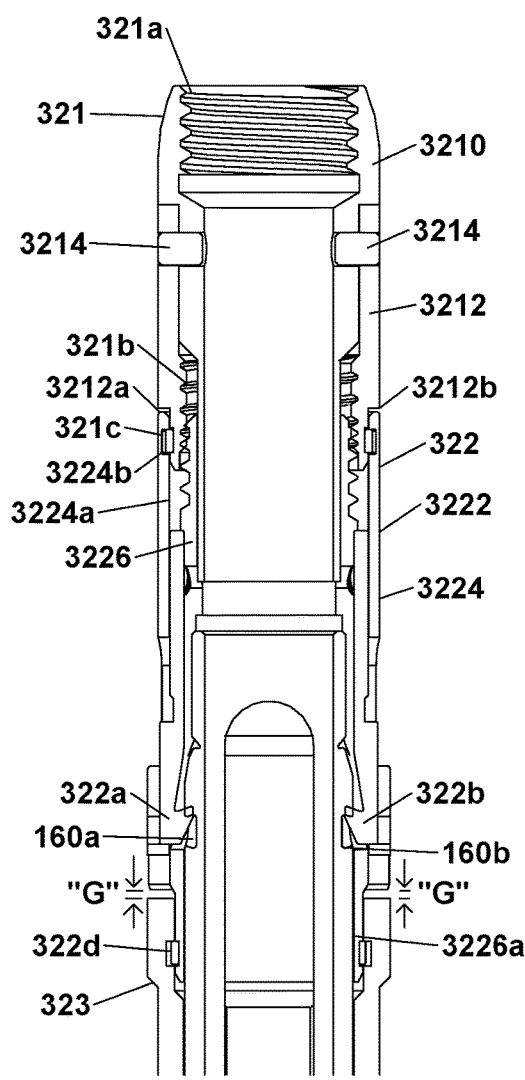
FIG. 8A
FIG. 8B

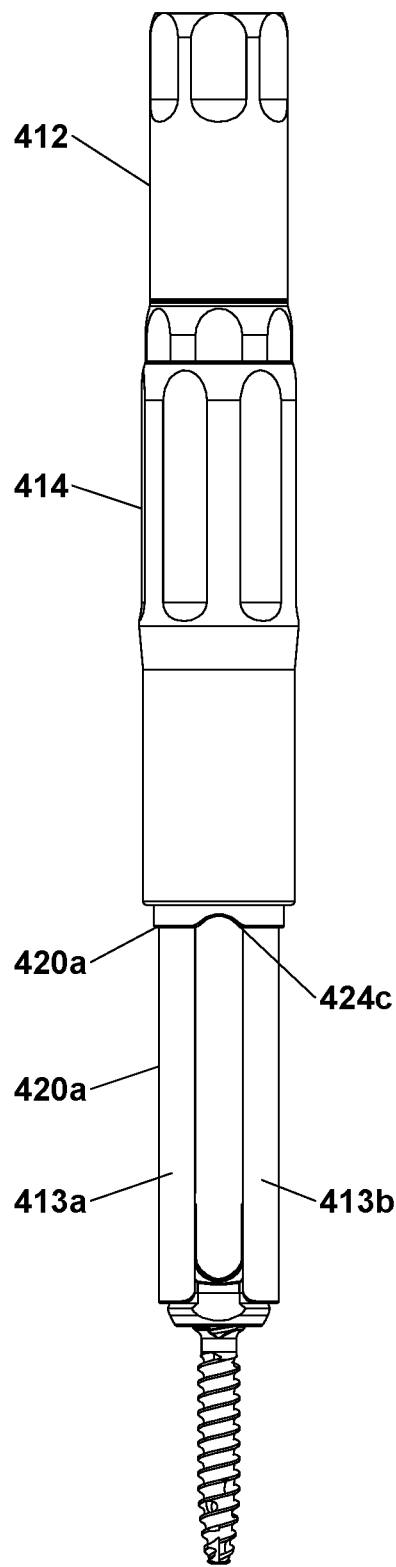
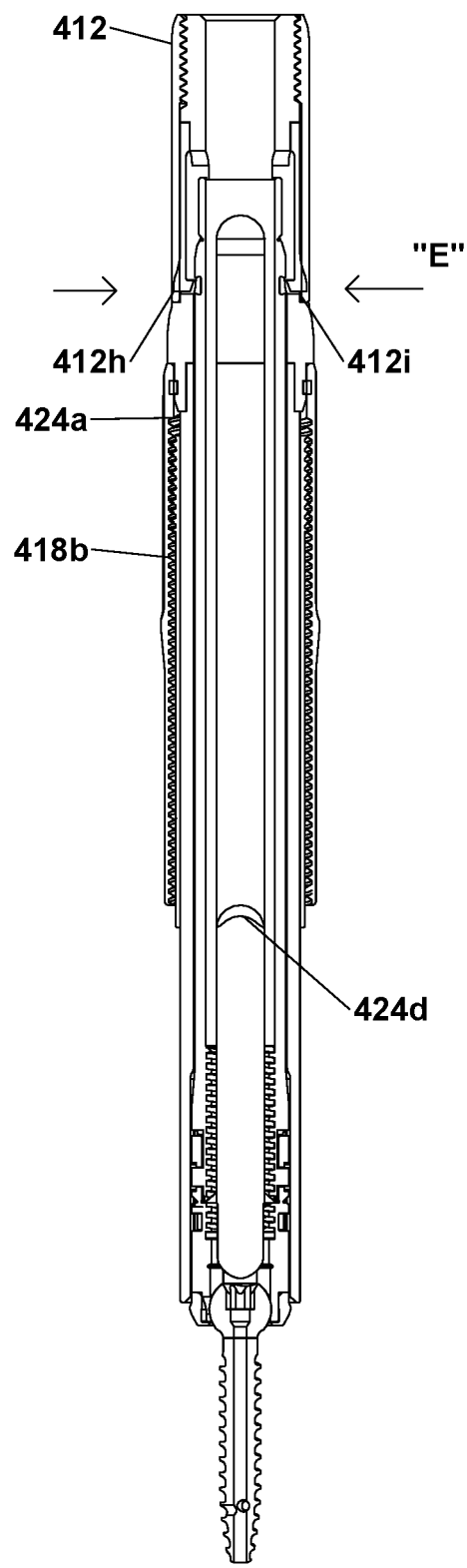
FIG. 17A
FIG. 17B

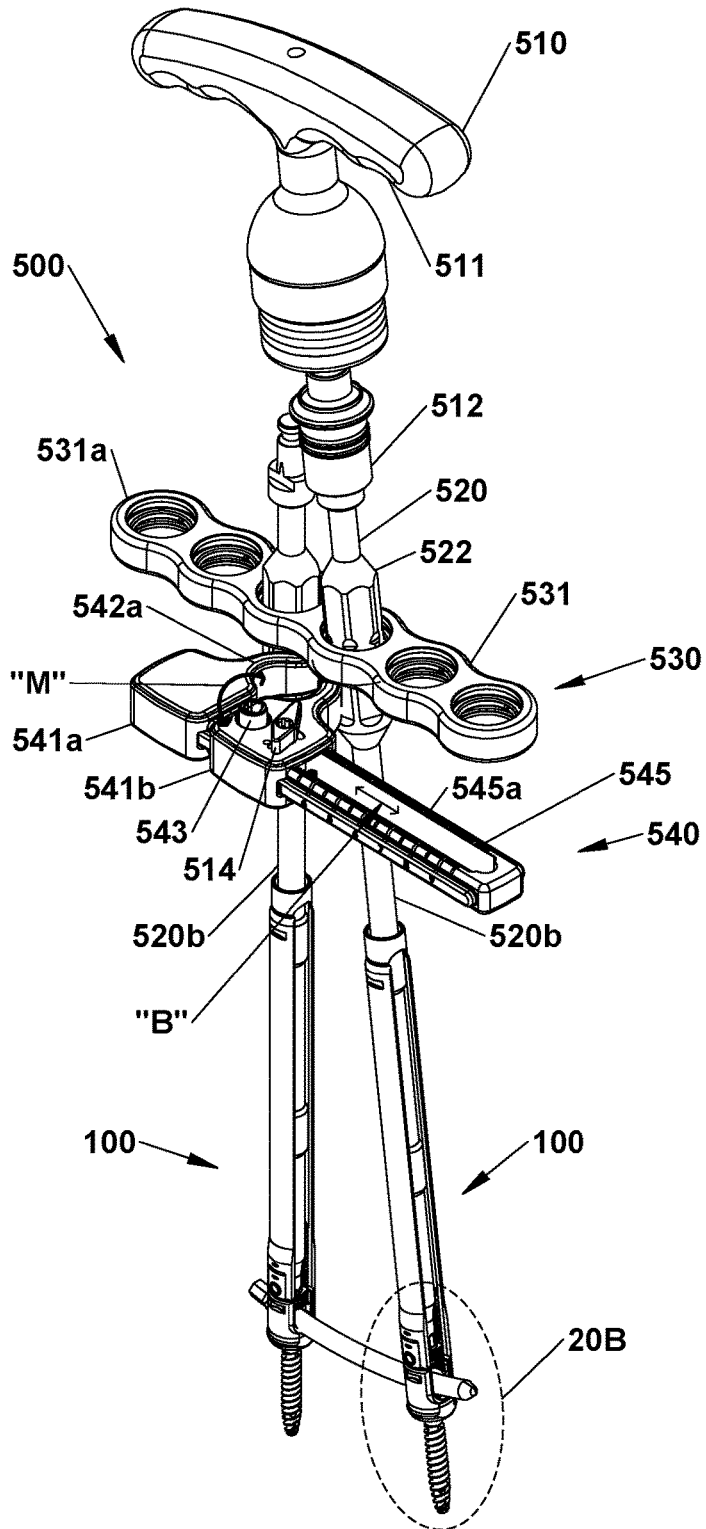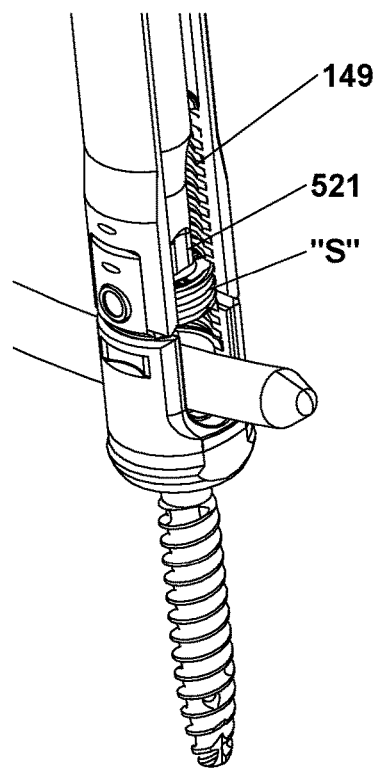
FIG. 20A
FIG. 20B

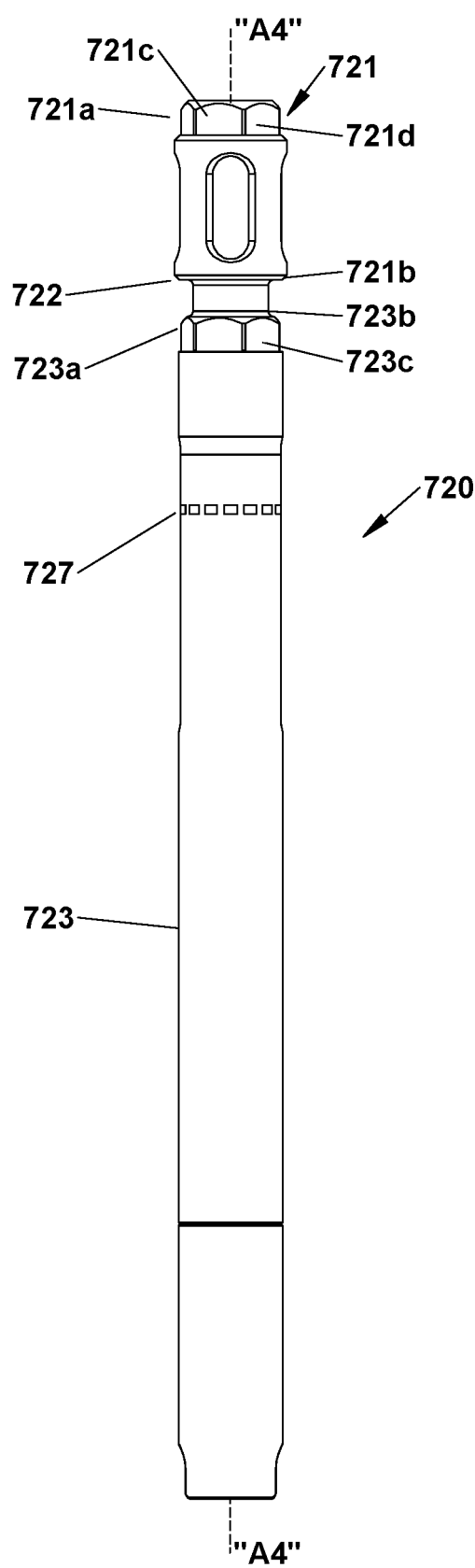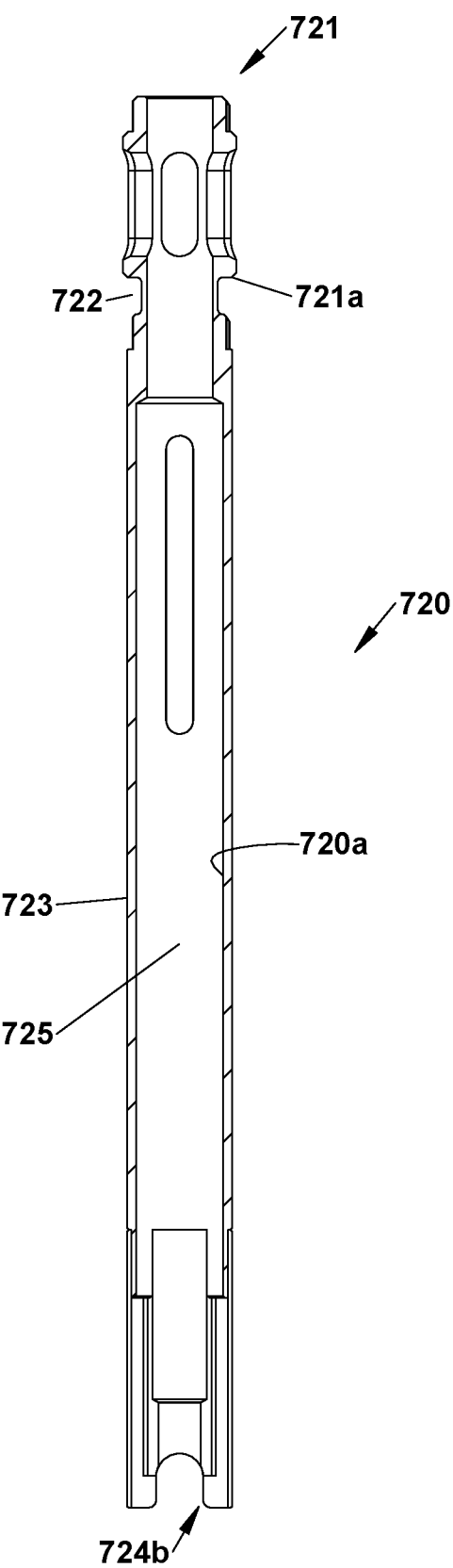
FIG. 24A
FIG. 24B

ROD REDUCER ASSEMBLY

CROSS-REFERENCE TO RELATED APPLICATION

This application is a divisional of U.S. application Ser. No. 15/850,169, filed on Dec. 21, 2017, which claims the benefit of U.S. Provisional Application Ser. No. 62/440,143, which was filed on Dec. 29, 2016, the entire contents of which are incorporated herein by reference.

TECHNICAL FIELD

The present disclosure relates to spinal surgery and, more particularly, to systems, devices, and methods for reducing spinal rods into pedicle screw housings and/or for manipulation of a spinal column.

BACKGROUND

The human spinal column or spine is a highly complex structure including twenty-four discrete bones, known as vertebrae, coupled sequentially to one another to house and protect critical elements of the body's nervous system. In between adjacent vertebrae of the spine are discs that function as vertebral shock absorbers for distributing pressure resulting from the impact of the body's activities.

Various disorders, diseases, and injuries can restrict the range of motion of the spine and/or interfere with important elements of the nervous system. Spinal fixation apparatus are widely employed in surgical procedures for correcting such spinal conditions. For example, spinal rods can be secured to the spine by spinal fixation fasteners, such as pedicle screws, to straighten abnormal curvature of the spine or to provide spinal stability.

It is desired to perform these procedures efficiently and in a minimally invasive manner.

SUMMARY

Accordingly, one aspect of the present disclosure is directed to a rod reducer assembly. The rod reducer assembly includes a pedicle screw housing that defines a rod-receiving recess and an extension assembly that extends from the pedicle screw housing. The extension assembly is coupled to the pedicle screw housing by a frangible member. The rod reducer assembly further includes a rod reducer. The rod reducer includes a knob and a sleeve assembly. The sleeve assembly includes an outer sleeve and an inner sleeve. The inner sleeve includes a finger that is selectively attachable to the extension assembly to secure the rod reducer to the extension assembly. The outer sleeve is axially movable relative to the inner sleeve to reduce a spinal rod into the rod-receiving recess of the pedicle screw housing in response to rotation of the knob relative to the sleeve assembly.

In some embodiments, the extension assembly may include a proximal portion defining a groove configured to receive the finger of the rod reducer to selectively attach the rod reducer to the extension assembly.

In certain embodiments, the knob may be coupled to the sleeve assembly by a retaining ring to enable the knob to rotate relative to the sleeve assembly.

In embodiments, the knob may be threadably coupled to the inner sleeve.

In some embodiments, the knob may be rotatable about the inner sleeve, which, in turn, causes axial translation of the knob and the outer sleeve relative to the inner sleeve.

In certain embodiments, the outer sleeve may be transitionable between an unreduced position and a reduced position. The rod reducer may be fixed to the extension assembly while the outer sleeve is disposed in the unreduced position. The rod reducer may be removable from the extension assembly while the outer sleeve is disposed in the reduced position.

According to another aspect, the present disclosure is directed to an assembly including a pedicle screw assembly, a derotation sleeve mountable to the pedicle screw assembly, and a rod reducer mountable to the derotation sleeve.

The pedicle screw assembly includes a screw securable to a spinal bone and a pedicle screw housing mounted to the screw. The pedicle screw housing defines a rod-receiving recess and includes an extension assembly coupled to the pedicle screw housing by a frangible member. The derotation sleeve is movable with the pedicle screw assembly to manipulate the spinal bone and is configured to inhibit the frangible member from breaking while manipulating the spinal bone. The rod reducer is mountable to the derotation sleeve and is configured to reduce a spinal rod into the rod-receiving recess of the pedicle screw.

In some embodiments, the derotation sleeve includes a locking mechanism positionable between a locked position and an unlocked position. The derotation sleeve may be movable with the pedicle screw assembly while in the locked position and may be separable from the pedicle screw assembly while in the unlocked position.

In certain embodiments, the derotation sleeve may include a knob, an upper shaft portion extending from the knob, and a lower shaft portion coupled to the upper shaft portion.

In embodiments, the upper shaft portion of the derotation sleeve may include a sleeve assembly including an inner sleeve and an outer sleeve. The inner sleeve may be selectively attachable to the extension assembly of the pedicle screw assembly to secure the derotation sleeve to the pedicle screw assembly.

In embodiments, the inner sleeve may include a finger and the extension assembly may define a groove configured to selectively receive the finger.

In certain embodiments, the knob may be rotatable relative to the inner sleeve to move the outer sleeve axially relative to the inner sleeve.

In some embodiments, the rod reducer may include a cap that is threadably engageable with the knob of the derotation sleeve to couple the rod reducer to the derotation sleeve.

In embodiments, the cap of the rod reducer may be coupled to a sleeve assembly of the rod reducer. The sleeve assembly of the rod reducer may include an outer sleeve and an inner sleeve. The outer sleeve of the rod reducer may be rotatable relative to the cap and the inner sleeve of the rod reducer to axially advance the inner sleeve of the rod reducer along the pedicle screw assembly and reduce the spinal rod into the rod-receiving recess of the pedicle screw housing of the pedicle screw assembly.

According to another aspect, the present disclosure is directed to a rod reducer assembly including a pedicle screw assembly and a rod reducer selectively mountable to the pedicle screw assembly.

The pedicle screw assembly includes a screw securable to a spinal bone, a pedicle screw housing mounted to the screw, and an extension assembly coupled to the pedicle screw housing by a frangible member. The pedicle screw housing defines a rod-receiving recess.

The rod reducer is selectively mountable to the pedicle screw assembly and includes a knob assembly and a reduction sleeve coupled to the knob assembly. The knob assembly includes an outer sleeve and an inner sleeve. The inner sleeve of the knob assembly is configured to selectively attach to the extension assembly. The reduction sleeve assembly includes a first inner sleeve and a second inner sleeve. The first inner sleeve is axially movable relative to the outer sleeve.

In embodiments, the second inner sleeve of the reduction sleeve may be coupled to the pedicle screw housing.

In some embodiments, the first inner sleeve may move axially relative to the second inner sleeve in response to rotation of the outer sleeve of the knob assembly relative to the first and second inner sleeves.

In certain embodiments, the inner sleeve of the knob assembly may include a finger that selectively couples to the extension assembly.

In embodiments, the outer sleeve of the knob assembly may be configured to compress the finger radially inward as the outer sleeve of the knob assembly moves relative to the inner sleeve of the knob assembly so that the finger secures the rod reducer to the pedicle screw assembly.

In some embodiments, the finger may be configured to bias radially outward when the outer sleeve of the knob assembly is spaced from the finger so that the rod reducer can separate from the pedicle screw assembly.

According to another aspect, the present disclosure is directed to a surgical system for manipulating a spinal bone. The surgical system includes a set screw and a first pedicle screw including a screw and a housing mounted to the screw. The screw is configured to secure the housing to spinal bone. The housing includes an internally threaded surface that defines a rod-receiving passage. The internally threaded surface is configured to receive the set screw and the rod-receiving passage is configured to receive a spinal rod.

The surgical system also includes a compression and distraction instrument configured to generate compressive or distractive forces and a first driving tool engageable with the compression and distraction instrument to receive compressive or distractive forces therefrom. The first driving tool is configured to rotate the set screw into the housing of the pedicle screw to partially lock the spinal rod in the housing of the first pedicle screw. The first driving tool is configured to impart compressive or distractive forces generated by the compression and distraction instrument to spinal bone while the spinal rod is partially locked in the housing. The first driving tool is configured to rotate the set screw relative to the housing of the first pedicle screw to fully lock the spinal rod in the housing while the compressive or distractive forces are imparted from the first driving tool to spinal bone.

In embodiments, an extension assembly may be coupled to the first pedicle screw housing by a frangible member and the first driving tool may be advanceable through the extension assembly to rotate the set screw.

In certain embodiments, a second pedicle screw may be configured to be inserted into a second spinal bone and to receive the spinal rod therein such that the first and second pedicle screws are configured to support the spinal rod across different spinal bones.

In embodiments, a second driving tool may be configured to be inserted into the second pedicle screw while the first driving tool is received within the first pedicle screw.

In some embodiments, a fulcrum may be provided and may include a body defining apertures. One or both of the first or second driving tools is receivable through one or more of the apertures to enable the body of the fulcrum to support one or both of the first or second driving tools relative to a respective one of the first or second pedicle screws.

In certain embodiments, the compression and distraction instrument may include a dial, a first body, and a second body disposed on the dial. The second body may be movable on the dial relative to the first body to generate compressive or distractive forces.

In embodiments, the first body and the second body of the compression and distraction instrument may be engageable with the first and second driving tools, respectively. As the second body moves relative to the first body, the compression and distraction instrument may enable the first and second driving tools to move a first portion of the spinal bone relative to a second portion of the spinal bone.

According to another aspect, the present disclosure is directed to a surgical system for installing a set screw into a pedicle screw assembly. The pedicle screw assembly includes a screw securable to a spinal bone, a pedicle screw housing mounted to the screw, and an extension assembly coupled to the pedicle screw housing by a frangible member. The pedicle screw housing includes an internally threaded surface that defines a rod-receiving recess. The internally threaded surface is configured to receive the set screw and the rod-receiving passage is configured to receive a spinal rod.

The surgical system further includes a support sleeve mountable to the pedicle screw assembly. The support sleeve is configured to inhibit the frangible member from breaking during rotation of the set screw into the pedicle screw housing. The support sleeve includes a recessed portion configured for engagement with an anti-torque tool to inhibit rotation of the support sleeve and the pedicle screw assembly as the set screw is rotated into the pedicle screw housing.

In accordance with another aspect of the present disclosure, there is provided a method of surgery including mounting a pedicle screw assembly to a vertebra, mounting a rod reducer on the pedicle screw assembly, placing a spinal rod adjacent a head assembly of the pedicle screw assembly, reducing the spinal rod into a rod-receiving passage of the pedicle screw assembly; and manipulating the rod reducer to break frangible members of the head assembly of the pedicle screw assembly in order to separate the head assembly from an extension assembly of the pedicle screw assembly. In particular, the pedicle screw assembly includes the head assembly, a screw extending distally from the head assembly, and the extension assembly extending proximally from the head assembly.

In an embodiment, mounting the rod reducer includes positioning the rod reducer over a proximal portion of the pedicle screw assembly.

In another embodiment, mounting the rod reducer includes engaging gripping fingers of the rod reducer with grooves defined in the extension assembly.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 3A is a front view of an embodiment of a rod reducer assembly shown in an unreduced position in accordance with the present disclosure;

FIG. 3B is a longitudinal, cross-sectional view of the rod reducer assembly of FIG. 3A;

FIG. 8A is a cross-sectional view of the derotation sleeve and pedicle screw assembly of FIGS. 6 and 7 and the locking mechanism of FIG. 7B shown in the unlocked position;

FIG. 8B is an enlarged, longitudinal, cross-sectional view of the indicated area of detail delineated in FIG. 8A;

FIG. 17A is a front view of the rod reducer assembly of FIG. 13, as depicted in FIG. 16;

FIG. 17B is a longitudinal, cross-sectional view of the rod reducer assembly of FIG. 13, as depicted in FIG. 17A;

FIG. 20A is perspective view of a surgical system including a distraction and compression instrument with the distraction and compression instrument shown coupled to the surgical system in a distraction mode in accordance with the present disclosure;

FIG. 20B is an enlarged view of the indicated area of detail delineated in FIG. 20A;

FIG. 24A is an enlarged side view of a sleeve of the surgical system of FIG. 23A;

FIG. 24B is a front, longitudinal, cross-sectional view of the sleeve of FIG. 24A;

DETAILED DESCRIPTION

Figure 1:
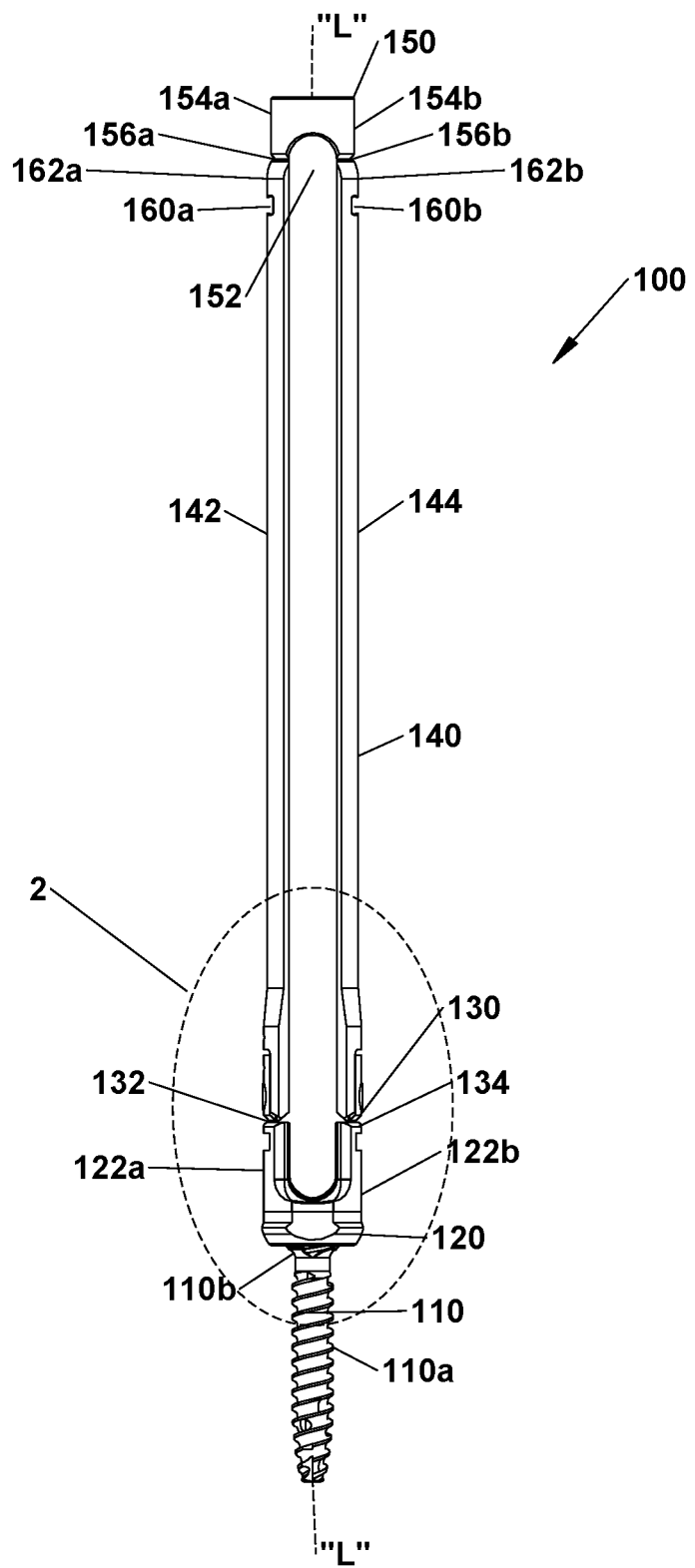
FIG. 1 is a front view of an embodiment of a pedicle screw assembly in accordance with the present disclosure.

Embodiments of the presently disclosed devices are described in detail with reference to the drawings, in which like reference numerals designate identical or corresponding elements in each of the several views. As used herein, the term "distal" or "leading" refers to that portion of the device that is farther from the user, while the term "proximal" or "trailing" refers to that portion of the device that is closer to the user. In addition, the term "cephalad" is known to indicate a direction toward a patient's head, whereas the term "caudad" indicates a direction toward the patient's feet. Further still, the term "lateral" is understood to indicate a direction toward a side of the body of the patient, i.e., away from the middle of the body of the patient. The term "posterior" indicates a direction toward the patient's back, and the term "anterior" indicates a direction toward the patient's front. As used herein, the term "clinician" refers to a doctor, nurse, or other care provider and may include support personnel. In the following description, well-known functions or constructions are not described in detail to avoid obscuring the present disclosure in unnecessary detail.

With reference to FIGS. 1-3B, a rod reducer assembly is shown and generally designated as 200. The rod reducer assembly 200 defines a longitudinal axis "A1-A1" and includes a pedicle screw assembly 100 and a rod reducer 202. The rod reducer 202 is positionable on the pedicle screw assembly 100 and configured to reduce the spinal rod "R" into a pedicle screw housing 120 of the pedicle screw assembly 100. For a detailed description of a similar rod reducer, reference can be made to U.S. Pat. App. Pub. No.

Figure 2:
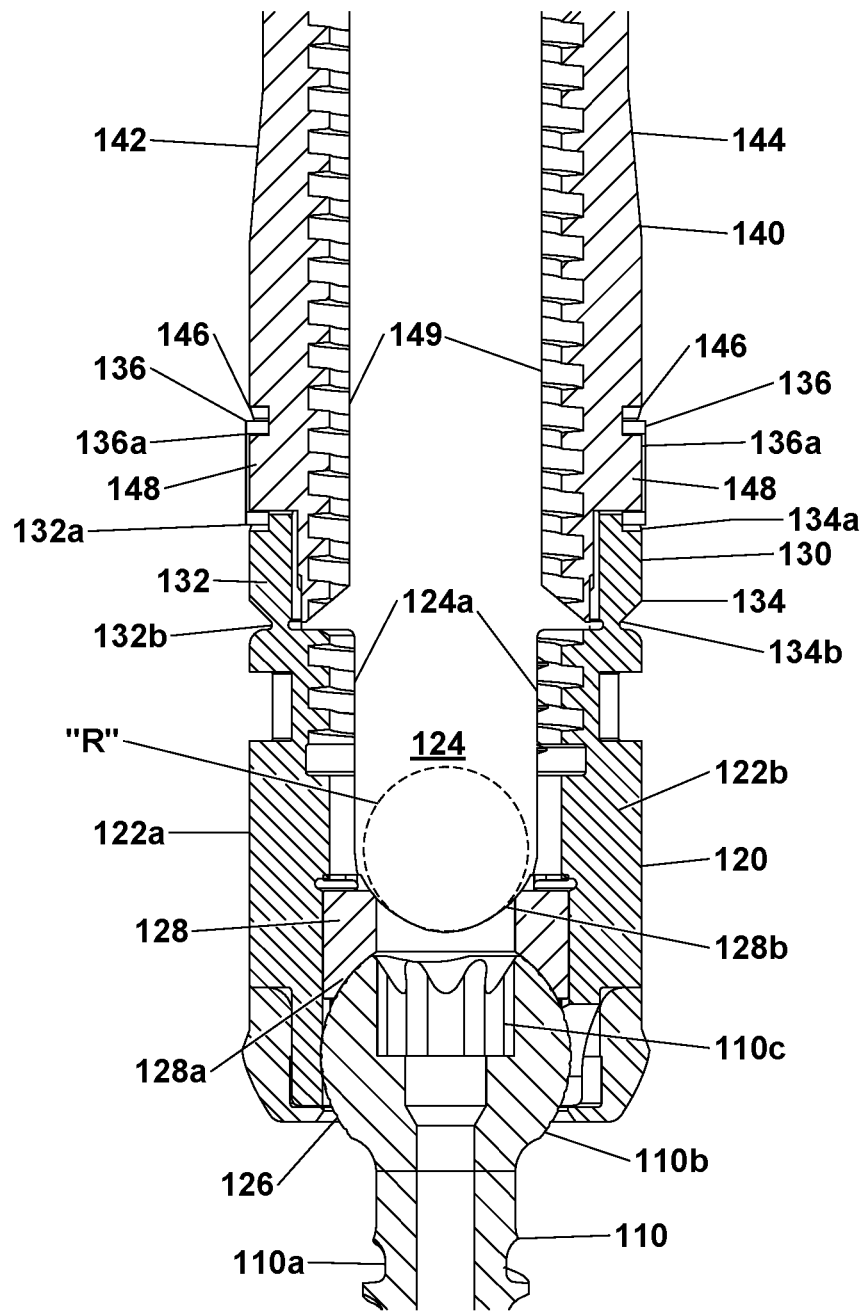
FIG. 2 is an enlarged, longitudinal, cross-sectional view of the indicated area of detail of FIG. 1.

2013/0046345, the entire contents of which are incorporated by reference herein. With particular reference to FIGS. 1 and 2, one embodiment of a pedicle screw assembly 100 defines a longitudinal axis "L-L" and includes a pedicle screw 110, a pedicle screw housing 120 supported on a proximal or trailing end of the pedicle screw 110, a tab assembly 130 extending proximally from the pedicle screw housing 120, an extension assembly 140 coupled to the tab assembly 130 and extending proximally therefrom, and a head assembly 150 coupled to a proximal end of the extension assembly 140.

The pedicle screw 110 of the pedicle screw assembly 100 has a threaded shank 110a and a head 110b supported on a proximal portion of the threaded shank 110a. The head 110b defines a drive recess 110c, which may be any suitable shape such as hexolobular or the like, that is configured to selectively receive a drive tool such as a screwdriver, e.g., driver 520 (FIG. 20A), to rotate the threaded shank 110a of the pedicle screw 110 into bone.

The pedicle screw housing 120 of the pedicle screw assembly 100 is U-shaped and includes a pair of wings or flanges 122a, 122b that defines a U-shaped rod-receiving passage 124 therethrough at a proximal end of the pedicle screw housing 120. The pair of flanges 122a, 122b defines a threaded internal surface 124a that is configured to threadably receive a set screw "S" (FIG. 20B) therein to engage and secure a spinal rod "R" (shown in phantom in FIG. 2) within the pedicle screw housing 120. The set screw "S" may be advanced into engagement with the spinal rod "R" via a rod inserter or driver, e.g., driver 520 (FIG. 20B). For a more detailed description of spinal rod insertion devices, reference can be made to, for example, International Application No. PCT/US16/46523, filed Aug. 11, 2016, the entire contents of which are incorporated by reference herein. The pedicle screw housing 120 further defines a concave recess 126 in a distal end thereof that receives the head 110b of the pedicle screw 110.

With particular reference to FIG. 2, the pedicle screw assembly 100 further includes an anvil 128 received within the pedicle screw housing 120. The anvil 128 defines a distal recess 128a that receives the proximal end of the head 110b of the pedicle screw 110, while the head 110b is disposed within the concave recess 126 of the pedicle screw housing 120. The anvil 128 further defines a saddle 128b on a proximal end thereof that supports the spinal rod "R" thereon. For a more detailed description of similar pedicle screw assemblies, reference can be made, for example, to U.S. Pat. No. 8,882,817, the entire contents of which are incorporated by reference herein.

The tab assembly 130 of the pedicle screw assembly 100 includes a pair of tabs 132, 134, that may be disposed in mirrored relation with one another. The tab 132 defines a recess 132a and includes a frangible member 132b secured to the flange 122a at a distal end of the tab 132. The tab 134 defines a recess 134a and includes a frangible member 134b secured to flange 122b at a distal end of the tab 134. The frangible members 132b, 134b may be integrally and/or monolithically formed with respective flanges 122a, 122b. The frangible members 132b, 134b may be configured to break upon application of a threshold force thereto (e.g., twisting, bending, tensile, and/or shear forces) to enable the tabs 132, 134 to separate from the flanges 122a, 122b. As used herein, the term "break" (or its equivalent) refers to rupturing, dividing, tearing, fracturing, splitting, and/or the like.

With continued reference to FIG. 2, the extension assembly 140 of the pedicle screw assembly 100 includes a pair of extensions 142, 144 coupled to the tabs 132, 134 of the pedicle screw assembly 100 by rings 136. More specifically, each of the pair of extensions 142, 144 defines a recess 146 in distal end portion thereof to receive one of the tabs 132, 134 of the tab assembly 130 and one of the rings 136 therein, respectively. A protuberance 148 extends from the recess 146 and is receivable through an opening 136a defined by the ring 136. Using any known securement technique such as welding, friction-fit, adhesion or the like, the rings 136 are secured about the protuberances 148 and within the recesses 146 of the extension assembly 140 and the recesses 132a, 134a of the tabs 132, 134, respectively, to couple the extension assembly 140 to the tabs 132, 134. The extension assembly 140 further includes an internal threaded surface 149 in vertical registration with the threaded internal surface 124a of the pedicle screw housing 120. The internal threaded surface 149 threadably receives the set screw "S" (FIG. 20B) and facilitates threaded reception of the set screw "S" into the pedicle screw housing 120 via the threaded internal surface 124a of the pedicle screw housing 120. Proximal portions of each of the pair of extensions 142, 144 define grooves 160a and 160b (FIG. 1) that are configured to facilitate selective attachment to various rod reducing instruments, as will be described in detail below. The grooves 160a, 160b may have any suitable shape such as circular and/or noncircular. The grooves 160a, 160 may be elongated in a direction transverse to the longitudinal axis "L-L" of the pedicle screw assembly 100. The proximal portions of each of the extensions 142, 144 further include outer camming surfaces 162a, 162b.

With brief reference back to FIG. 1, the head assembly 150 of the pedicle screw assembly 100 defines a recess 152 having an inverted U-shape that separates a pair of arms 154a, 154b of the head assembly 150. Distal ends of the pair of arms 154a, 154b are coupled to proximal ends of the extensions 142, 144 of the extension assembly 140 by the frangible members 156a, 156b. Similar to the frangible members 132b, 134b of the tab assembly 130, the frangible members 156a, 156b of the head assembly 150 are configured to break upon application of a threshold force thereto to separate the head assembly 150 from the extension assembly 140 as desired, for example, with a pair of pliers as detailed in International Application No. PCT/US16/46523 incorporated herein by reference above.

With particular reference to FIGS. 3A and 3B, the rod reducer 202 of the rod reducer assembly 200 has a knob or cap 204 having a distal portion that is rotatably connected to a proximal portion of a sleeve assembly 206 of the rod reducer 202. The cap 204 of the rod reducer 202 includes an outer surface 204a and a threaded internal surface 204b that defines a central opening 204c through the cap 204. The outer surface 204a of the cap 204 further includes a drive surface 204d configured to impart axial drive force, as indicated by arrows "Y" (FIG. 4A), onto the sleeve assembly 206 in response to rotation of the cap 204, as indicated by arrows "Z," about the longitudinal axis "A1-A1" (e.g., clockwise and/or counterclockwise) of the rod reducer assembly 200 relative to the sleeve assembly 206.

The sleeve assembly 206 of the rod reducer assembly 200 includes an inner sleeve 208, an outer sleeve 210 and a retaining ring 212 secured to an inner surface of the outer sleeve 210 adjacent to the inner sleeve 208. The inner sleeve 208 of the sleeve assembly 206 includes a threaded external surface 208a on a proximal end portion thereof and gripping fingers 208b, 208c on a distal end portion thereof. The gripping fingers 208b, 208c of the inner sleeve 208 may be in the form of hooks. The threaded external surface 208a of the inner sleeve 208 is configured to threadably engage the threaded internal surface 204b of the cap 204 to facilitate rotation of the cap 204 relative to the sleeve assembly 206. The gripping fingers 208b, 208c of the inner sleeve 208 are configured to engage the grooves 160a and 160b of the pedicle screw assembly 100 to rotationally fix the inner sleeve 208 to the pedicle screw assembly 100, thereby fixing the rod reducer 202 to the pedicle screw assembly 100. The gripping fingers 208b, 208c may be flexible to facilitate a snap-fit engagement into the grooves 160a and 160b of the pedicle screw assembly 100.

The outer sleeve 210 of the sleeve assembly 206 is in contacting relation with the drive surface 204d of the cap 204 and positioned to surround the inner sleeve 208 and the distal portion of the cap 204. The outer sleeve 210 includes a proximal portion 210a and a distal portion 210b. The distal portion 210b of the outer sleeve 210 defines one or more rod-engaging recesses 210c configured to engage the spinal rod "R." Each of the rod-engaging recesses 210c may have an inverted U-shaped configuration. The proximal portion 210a of the outer sleeve 210 is positioned to receive the distal portion of the cap 204 to enable the cap 204 to rotate relative to the outer sleeve 210. The outer sleeve 210 further defines longitudinal slots 210d, 210e that receive the gripping fingers 208b, 208c of the inner sleeve 208 therein. The longitudinal slots 210d, 210e are positioned to slide along the gripping fingers 208b, 208c of the outer sleeve 210 to enable the outer sleeve 210 to slide axially relative to the inner sleeve 208 in response to rotation of the cap 204 relative to the sleeve assembly 206.

In operation, the pedicle screw assembly 100 of the rod reducer assembly 200 is mounted to a vertebra (e.g., screwed in to the vertebra) of a spine (not shown) so that the rod reducer 202 of the rod reducer assembly 200 can be mounted on the pedicle screw assembly 100 as seen in FIGS. 3A and 3B. To mount the rod reducer 202 to the pedicle screw assembly 100, the rod reducer 202 is positioned over the proximal portion of the pedicle screw assembly 100 and advanced distally along the pedicle screw assembly 100. As the rod reducer 202 is advanced distally, the gripping fingers 208b, 208c of the rod reducer 202 engage and cam along the camming surfaces 162a, 162b of the extension assembly 140 of the pedicle screw assembly 100. The camming surfaces 162a, 162b of the pedicle screw assembly 100 are configured to urge or flex the gripping fingers 208b, 208c of the rod reducer 202 radially outward as the gripping fingers 208b, 208c are advanced distally therealong until the gripping fingers 208b, 208c of the of the rod reducer 202 snap radially inward and into the grooves 160a, 160b of the extension assembly 140 of the pedicle screw assembly 100. Engagement of the gripping fingers 208b, 208c of the rod reducer 202 and the grooves 160a, 160b of the extension assembly 140 of the pedicle screw assembly 100 locks the rod reducer 202 onto the pedicle screw assembly 100. With the gripping fingers 208b, 208c of the rod reducer 202 secured to the grooves 160a, 160b of the extension assembly 140, the inner sleeve 208 of the rod reducer 202 is axially fixed onto the proximal portion of the pedicle screw assembly 100.

Figure 4A:
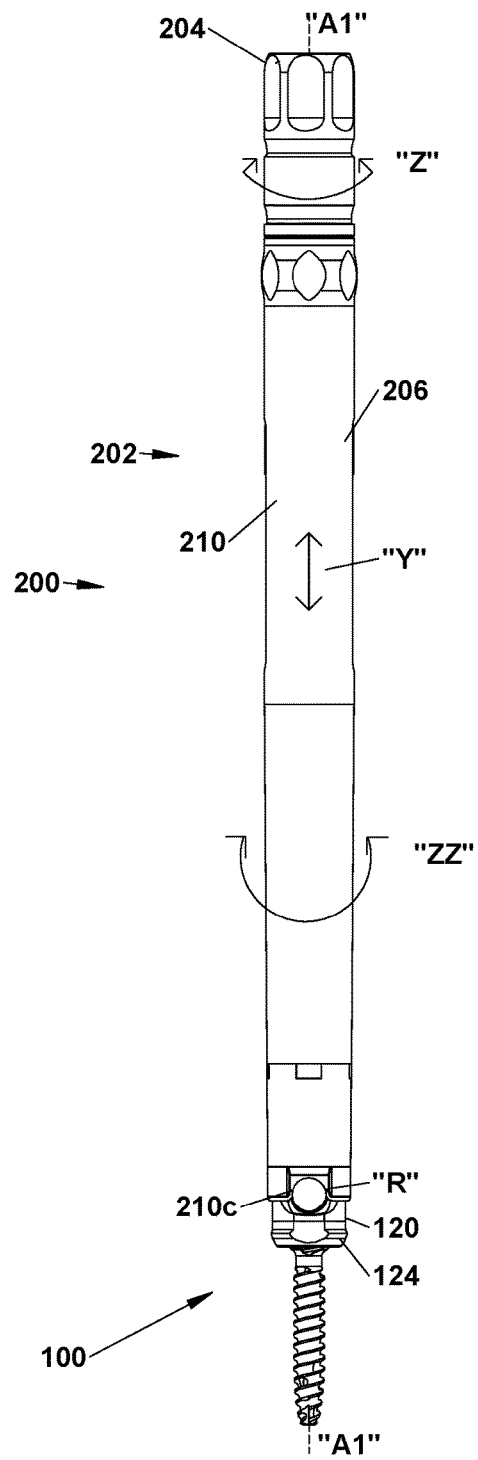
FIG. 4A is a front view of the embodiment of the rod reducer assembly of FIG. 3A shown in a reduced position.
Figure 4B:
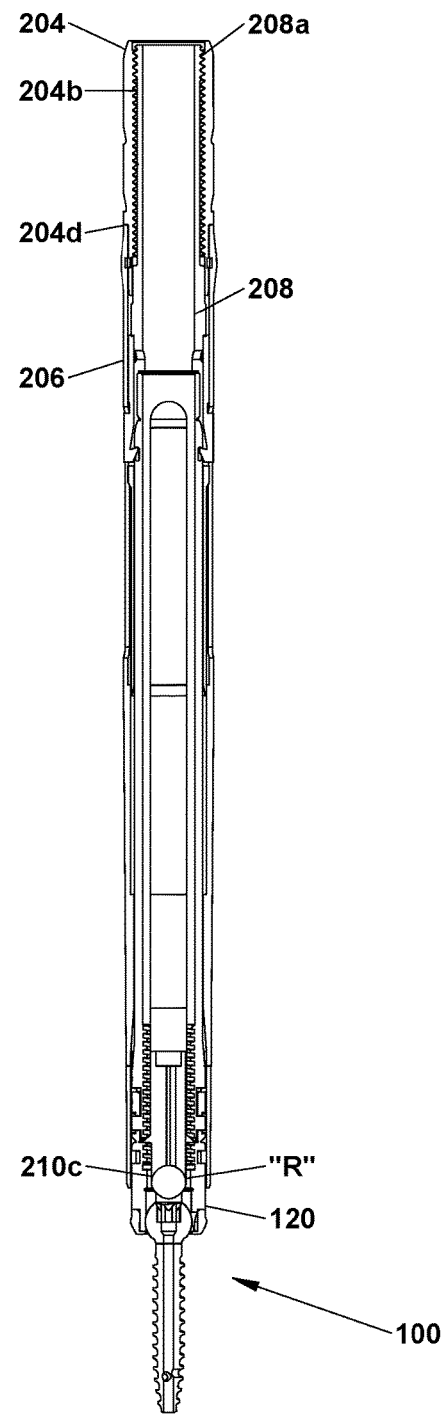
FIG. 4B is a longitudinal, cross-sectional view of the rod reducer assembly of FIG. 4A.

Referring now to FIGS. 1-4B, with the spinal rod "R" positioned within the rod-receiving passage 124 of the pedicle screw assembly 100, and the rod reducer 202 locked onto the pedicle screw assembly 100, the cap 204 of the rod reducer 202 is rotatable (e.g., clockwise and/or counterclockwise) relative to sleeve assembly 206 of the rod reducer 202 to impart axial force onto the sleeve assembly 206 through the drive surface 204d of the cap 204. In particular, rotation of the cap 204 (e.g., clockwise and/or counterclockwise) relative to the sleeve assembly 206, as indicated by arrow "Z," axially moves the outer sleeve 210 of the sleeve assembly 206, as indicated by arrow "Y," along the longitudinal axis "A1-A1" of the rod reducer assembly 200, and relative to the inner sleeve 208 of the sleeve assembly 206 (and relative to the pedicle screw assembly 100), from a proximal or unreduced position (FIGS. 3A and 3B) to a distal or reduced position (FIGS. 4A and 4B).

As the outer sleeve 210 of the rod reducer 202 is advanced distally relative to the pedicle screw assembly 100, the rod-engaging recesses 210c of the outer sleeve 210 engage the spinal rod "R" to reduce the spinal rod "R" into the pedicle screw housing 120 of pedicle screw assembly 100 as the outer sleeve 210 moves from the unreduced position to the reduced position.

In the reduced position of the outer sleeve 210 of the rod reducer 200, the outer sleeve 210 supports or stabilizes the frangible members 132b, 134b, 156a, 156b of the pedicle screw assembly 100 (see FIGS. 1 and 2) so that the rod reducer assembly 200 can be manipulated (e.g., in one or more caudad, cephalad, posterior, anterior, and/or lateral directions) to selectively position and/or reposition the rod reducer assembly 200, the spinal column, and/or portions of the spinal column as desired.

By virtue of the structural arrangement of one or more of the components of the rod reducer assembly 200 and/or the rigidity thereof, the rod reducer assembly 200 is configured to reinforce the pedicle screw assembly 100, extension assembly 140, the tab assembly 130, and/or the head assembly 150 by limiting forces (e.g., twisting, bending, flexing, tensile, and/or shear forces) from being applied (e.g. directly) to the frangible members 132b, 134b of the pedicle screw assembly 100 and/or to the frangible members 156a, 156b of the head assembly 150 (e.g., in one or more caudad, cephalad, posterior, anterior, and/or lateral directions). Instead, the rod reducer assembly 200 and/or components thereof, are configured to absorb these forces and inhibit the tabs 132, 134 of the tab assembly 130 from prematurely separating from the flanges 122a, 122b of the pedicle screw housing 120 and/or the head assembly 150 from prematurely separating from the extension assembly 140.

Once the rod reducer assembly 200 is positioned as desired, the cap 204 of the rod reducer 202 can be rotated to move the outer sleeve 210 of the sleeve assembly 206 of the rod reducer 202 to a proximal position (see, e.g., FIG. 3A) that is proximal of the frangible members 132b, 134b of the pedicle screw assembly 100. In such a proximal position, lateral movement of the rod reducer 202 to a breaking threshold angle "a" (e.g., from about 1 degree to about 20 degrees) relative to the pedicle screw assembly 100 will break the frangible members 132b, 134b and separate the rod reducer 202, the head assembly 150, the extension assembly 140, and the tab assembly 130 from the pedicle screw housing 120 of the pedicle screw assembly 100.

Alternatively, to separate the rod reducer 202 from the pedicle screw assembly 100 without breaking the frangible members 132b, 134b of the pedicle screw assembly 100, the rod reducer 202 can be rotated relative to the pedicle screw assembly 100 while the rod reducer 202 is disposed in the reduced position. In the reduced position, the fingers 208b, 208c of the rod reducer 202 are configured to cam out of the grooves 160a, 160b of the extension assembly 140 as the rod reducer 202 is rotated about the longitudinal axis "L-L" of the pedicle screw assembly 100 and relative to the pedicle screw assembly 100, as indicated by arrows "ZZ" (FIG. 4A). Once the rod reducer 202 is separated from the pedicle screw assembly 100, the head assembly 150, the extension assembly 140, and/or the tab assembly 130 of the pedicle screw assembly 100 can then be separated or otherwise broken from the pedicle screw housing 120 of the pedicle screw assembly 100 using various instruments (not shown) such as those described in International Application No. PCT/US16/46523, entire contents of which are incorporated by reference herein.

Figure 5:
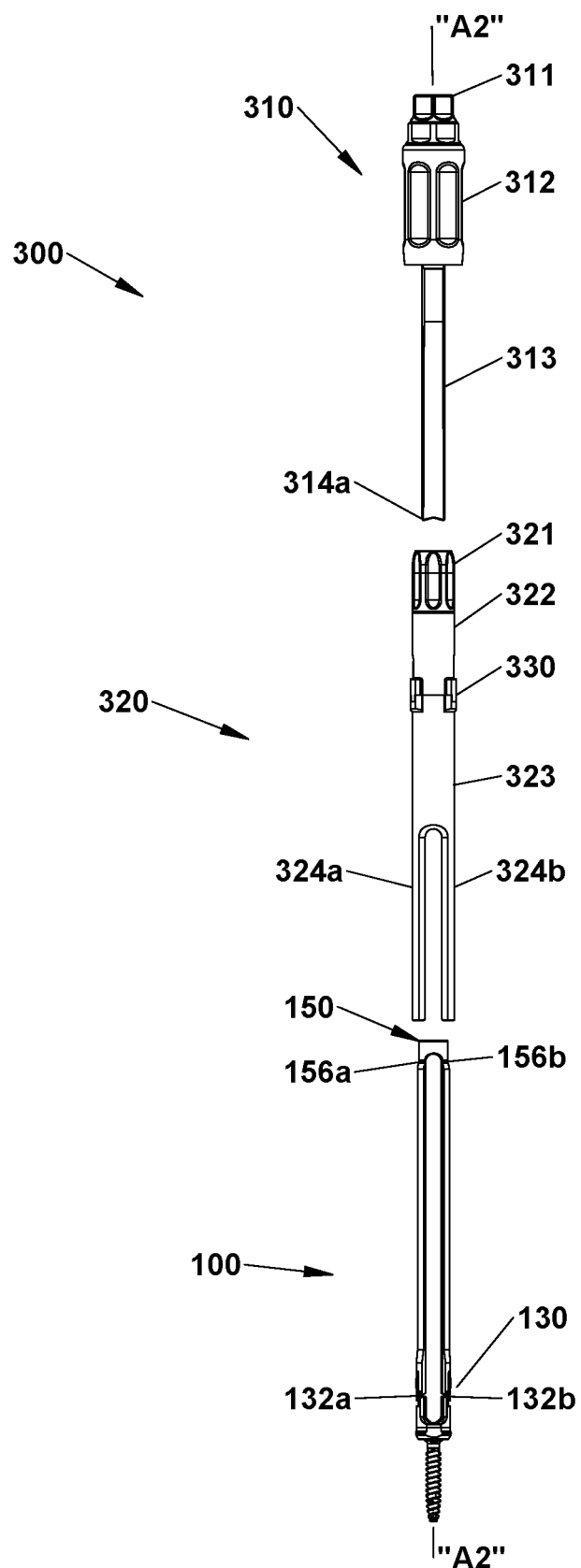
FIG. 5 is a front view, with parts separated, of another embodiment of a rod reducer assembly in accordance with the present disclosure.

With reference to FIGS. 1, 2, and 5, a rod reducer assembly in accordance with another embodiment of the present disclosure is shown and generally designated as 300. The rod reducer assembly 300 defines a longitudinal axis "A2-A2" and generally includes the pedicle screw assembly 100, a rod reducer 310, and a derotation sleeve 320. The rod reducer 310 may be used to reduce a spinal rod "R" into the pedicle screw housing 120 of the pedicle screw assembly 100 and the derotation sleeve 320 may be used to manipulate the spine while inhibiting the frangible members 132b, 134b and 156a, 156b of the tab and head assemblies 130, 150 of the pedicle screw assembly 100, respectively, from breaking, similar to that described above with respect to the rod reducer assembly 200.

With reference now to FIGS. 6-10B, the derotation sleeve 320 of the rod reducer assembly 300 includes a knob 321, an upper shaft portion 322 extending distally from the knob 321, a lower shaft portion 323 extending distally from the upper shaft portion 322, and a locking mechanism 330 supported between the upper and lower shaft portions 322, 323 for selectively locking the upper and lower shaft portions 322, 323 together.

Figure 6:
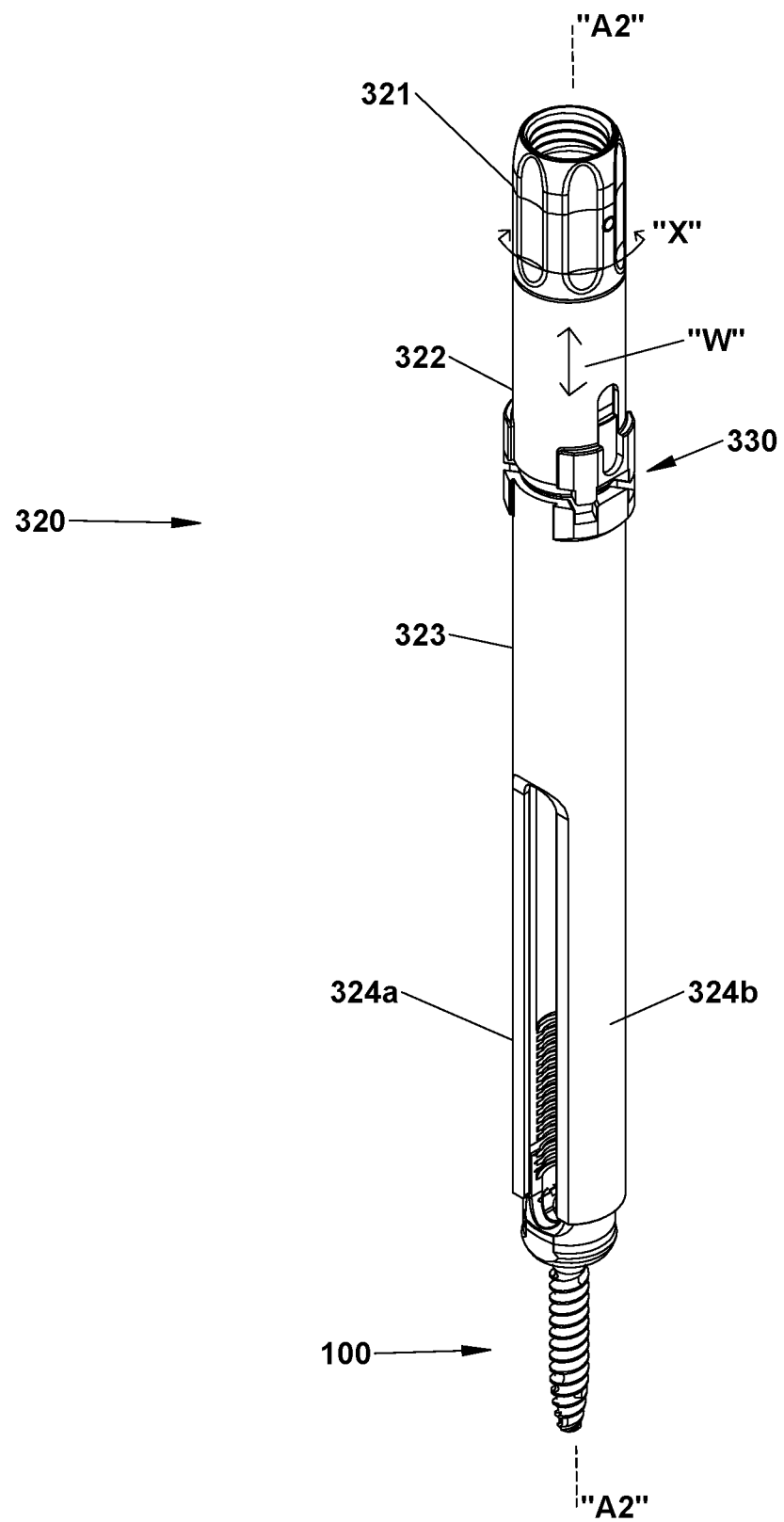
FIG. 6 is a perspective view of a derotation sleeve of the rod reducer assembly of FIG. 5 positioned on a pedicle screw assembly of the rod reducer assembly of FIG. 5.

The knob 321 of the derotation sleeve 320 includes a first portion 3210 and a second portion 3212 that are pinned together by pins 3214. The first portion 3210 of the knob 321 includes an internal threaded surface 321a configured to threadably receive the rod reducer 310 (FIG. 5). The second portion 3212 of the knob 321 includes and an internal threaded surface 321b configured to threadably engage the upper shaft portion 322 of the derotation sleeve 320. The second portion 3212 of the knob 321 also includes an outer surface 3212a that defines a slot 3212b therein. The second portion 3212 of the knob 321 is rotatably connected to the upper shaft portion 322 by a retaining ring 321c. The retaining ring 321c is positioned between the knob 321 of the derotation sleeve 320 and the upper shaft portion 322 of the derotation sleeve 320 to enable the knob 321 to rotate about the upper shaft portion 322 (e.g., clockwise and/or counterclockwise), as indicated by arrows "X" (FIG. 6).

The upper shaft portion 322 of the derotation sleeve 320 includes a sleeve assembly 3222 having an outer sleeve 3224 and an inner sleeve 3226. The outer sleeve 3224 includes an inner surface 3224a defining a slot 3224b that receives the retaining ring 321c therein. The outer sleeve 3224 is positioned to move axially, as indicated arrows "W" (FIG. 6), along the longitudinal axis "A2-A2" of the rod reducer assembly 300 and relative to the inner sleeve 3226 in response to rotation of the knob 321 of the derotation sleeve 320. The outer sleeve 3224 further includes teeth 331 that extend distally from the outer sleeve 3224.

The inner sleeve 3226 of the sleeve assembly 3222 includes threads 322c on a proximal outer surface thereof. The threads 322c (FIG. 10B) of the inner sleeve 3226 are disposed in threaded engagement with the internal threaded surface 321b of the knob 321. The inner sleeve 3226 of sleeve assembly 3222 further includes fingers 322a, 322b that are selectively engagable with the grooves 160a, 160b of the extension assembly 140 of the pedicle screw assembly 100, similar to the fingers 208b, 208c of the rod reducer assembly 200 described above. The inner sleeve 3226 of the sleeve assembly 3222 includes a distal portion 3226a that is received within a proximal portion of the lower shaft portion 323 of the derotation sleeve 320. The inner sleeve 3226 of the sleeve assembly 3222 is selectively rotatably connected to the lower shaft portion 323 by a retaining ring 322d. The retaining ring 322d is configured to enable the upper shaft portion 322 of the derotation sleeve 320 to rotate about the longitudinal axis "A2-A2" (e.g., clockwise and/or counterclockwise) relative to the lower shaft portion 323, as indicated by arrows "V" (FIG. 7A), when the locking mechanism 330 is disposed in an unlocked position (FIG. 7A) for rotatably separating the fingers 322a, 322b of the sleeve assembly 3222 from the grooves 160a, 160b of extension assembly 140 of pedicle screw assembly 100 (see FIGS. 8A and 8B).

The lower shaft portion 323 of the derotation sleeve 320 defines recesses 332 at a proximal end thereof configured for engagement with the plurality of teeth 331 of the upper shaft portion 322 of the derotation sleeve 320. The lower shaft portion 323 further includes first and second legs 324a, 324b which are positionable about the pedicle screw assembly 100 adjacent to the frangible members 132b, 134b to stabilize and/or support the frangible members 132b, 134b for inhibiting premature breaking of the frangible members 132b, 134b during manipulation and/or derotation of the spinal column with the derotation sleeve 320 and the pedicle screw assembly 100 coupled together.

By virtue of the structural arrangement of one or more of the components of the rod reducer assembly 300 and/or the rigidity thereof, the rod reducer assembly 300 is configured to reinforce the pedicle screw assembly 100, extension assembly 140, the tab assembly 130, and/or the head assembly 150 by limiting forces (e.g., twisting, bending, flexing, tensile, and/or shear forces) from being applied (e.g. directly) to the frangible members 132b, 134b of the pedicle screw assembly 100 and/or to the frangible members 156a, 156b of the head assembly 150 (e.g., in one or more caudad, cephalad, posterior, anterior, and/or lateral directions). Instead, the rod reducer assembly 300 and/or components thereof, are configured to absorb these forces and inhibit the tabs 132, 134 of the tab assembly 130 from prematurely separating from the flanges 122a, 122b of the pedicle screw housing 120 and/or the head assembly 150 from prematurely separating from the extension assembly 140.

Figure 7A:
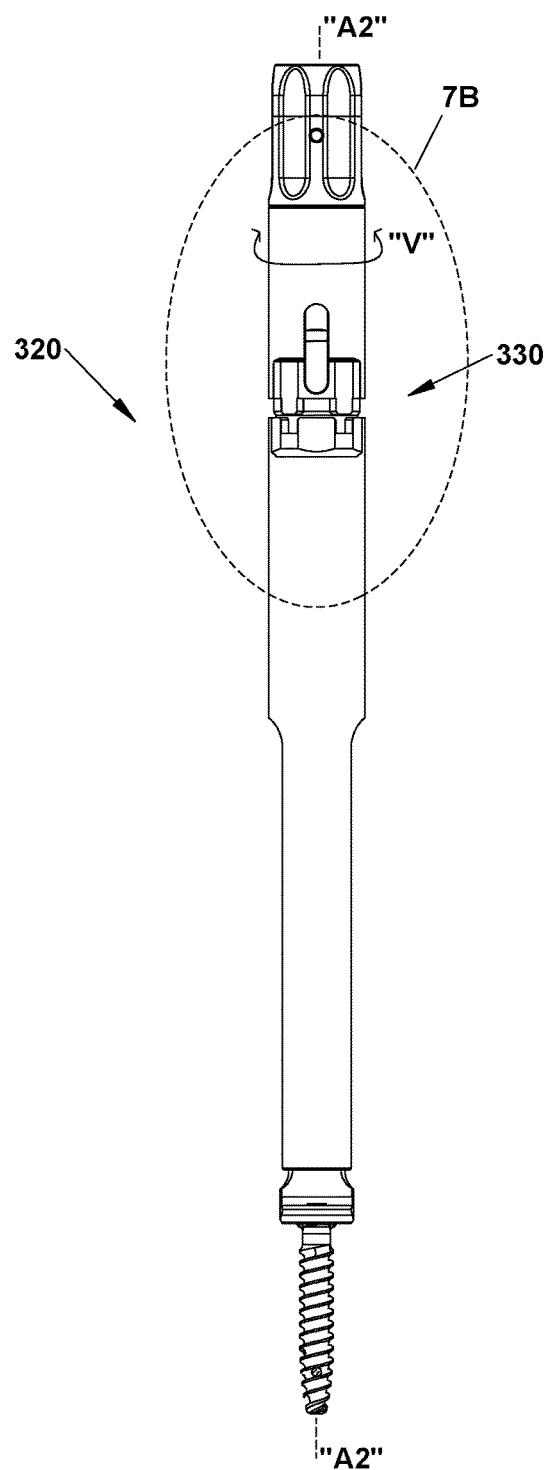
FIG. 7A is a side view of the derotation sleeve and pedicle screw assembly of FIG. 6.
Figure 7B:
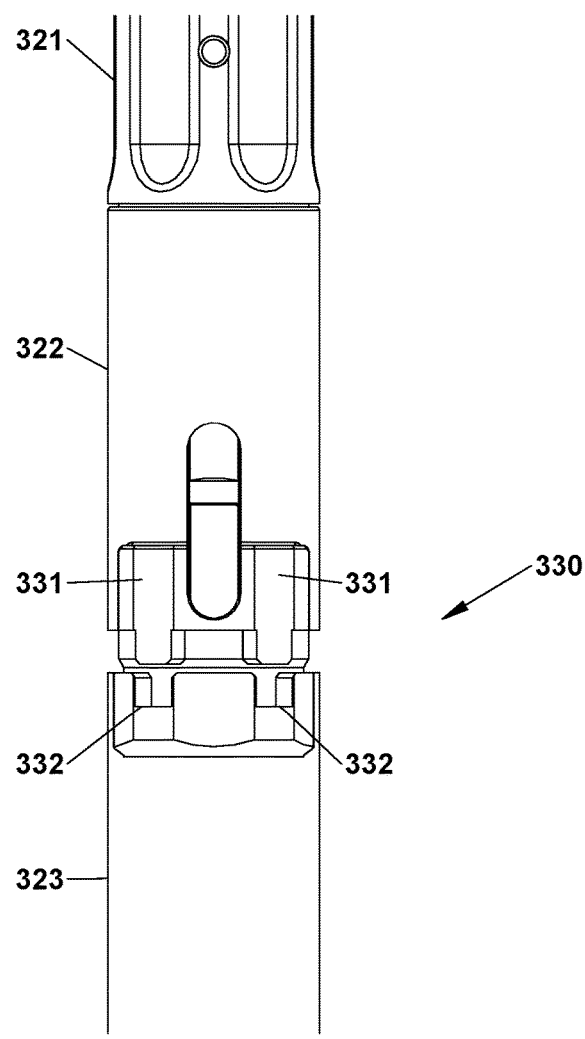
FIG. 7B is an enlarged view of a locking mechanism of the derotation sleeve of FIGS. 5 and 6 shown in an unlocked position.
Figure 9A:
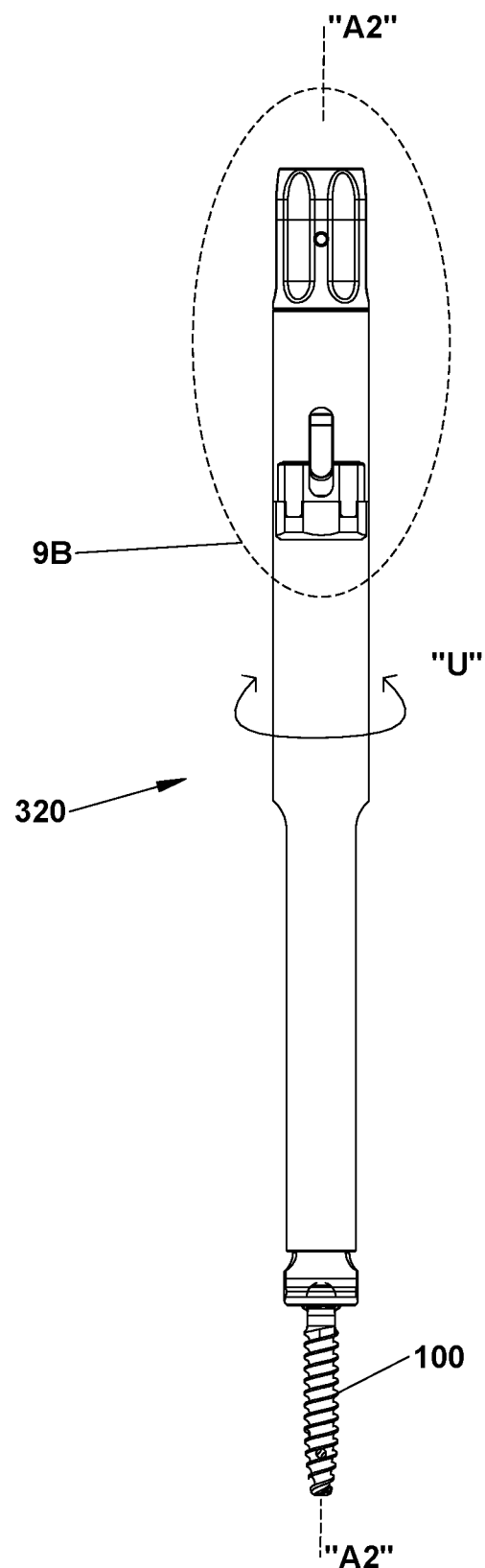
FIG. 9A is a side view of the derotation sleeve and pedicle screw assembly of FIGS. 5 and 6 with the locking mechanism of FIG. 7B shown in a locked position.
Figure 9B:
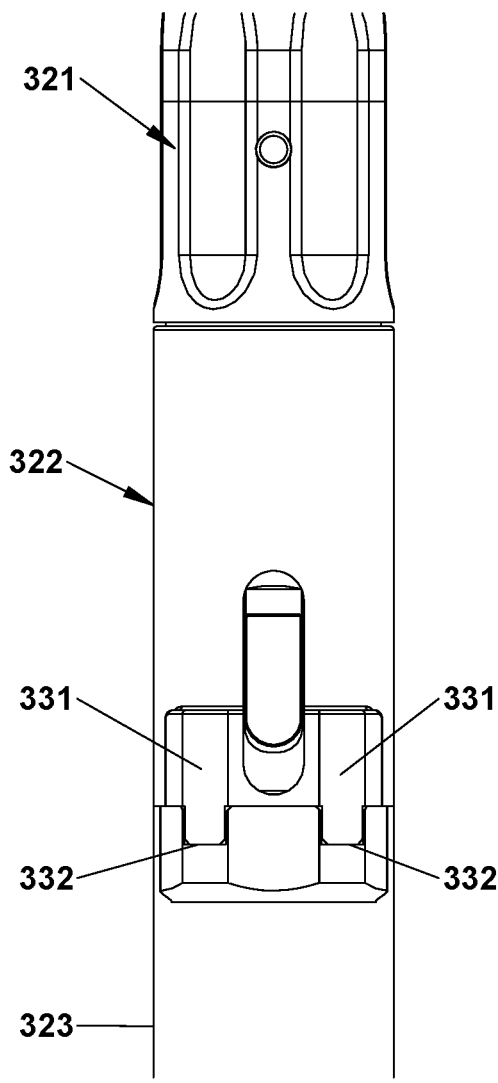
FIG. 9B is an enlarged view of the indicated area of detail delineated in FIG. 9A.
Figure 10A:
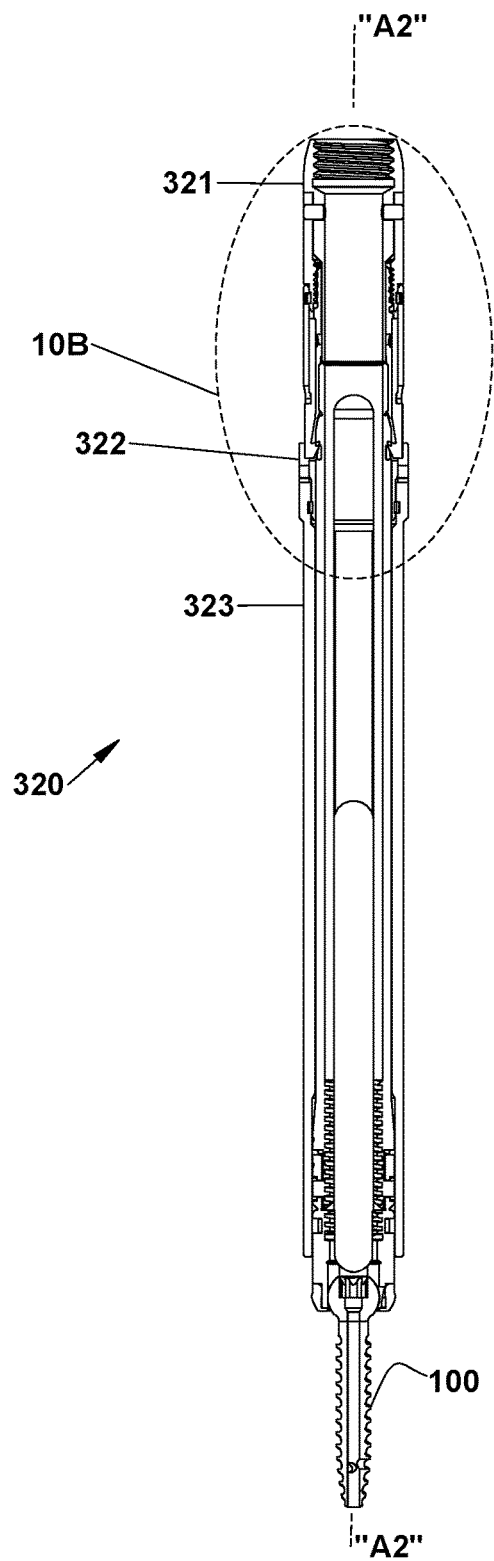
FIG. 10A is a longitudinal, cross-sectional view of the derotation sleeve and pedicle screw assembly of FIGS. 5 and 6 with the locking mechanism of FIG. 7B shown in the locked position.
Figure 10B:
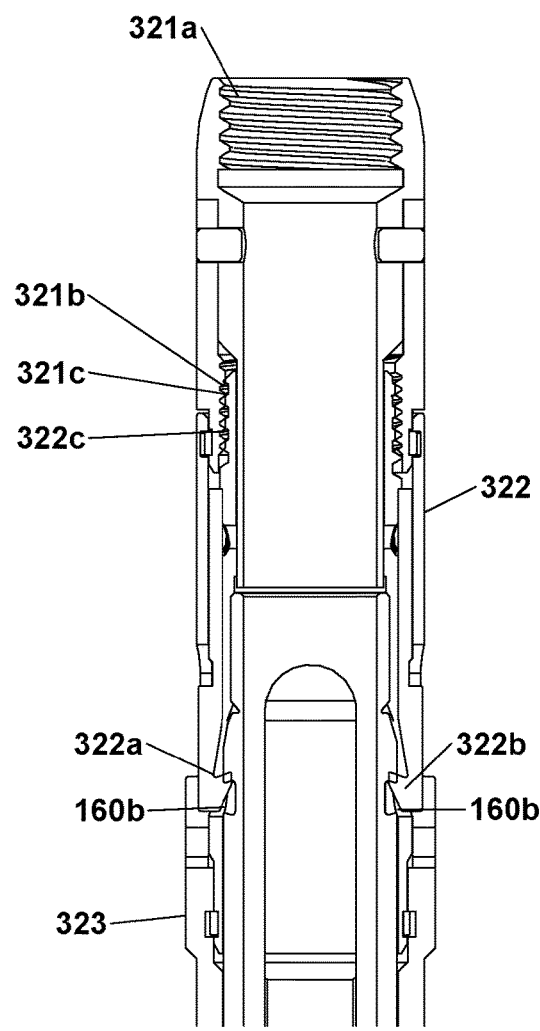
FIG. 10B is an enlarged view of the indicated area of detail delineated in FIG. 10A.

With reference to FIG. 7B, the locking mechanism 330 of the derotation assembly 320 includes the teeth 331 of the upper shaft portion 322 of the derotation assembly 300 and the recesses 332 of the lower shaft portion 323 of the derotation assembly 300. The locking mechanism 330 is positionable between an unlocked position (FIG. 7B) and a locked position (FIG. 9B). In the unlocked position of the locking mechanism 330, the teeth 331 of the locking mechanism 330 are spaced apart from the recesses 332 of the locking mechanism 330 by a gap "G" (FIG. 8B) so that the upper shaft portion 322 can rotate relative to the lower shaft portion 323 to enable the derotation assembly 300 to separate from the pedicle screw assembly 100. In the locked position of the locking mechanism 330, the teeth 331 and the recesses 332 are engaged so that the fingers 322a, 322b (FIG. 8B) of the sleeve assembly 3222 remain engaged within the grooves 160a, 160b of extension assembly 140 and the derotation assembly 320 and the pedicle screw assembly 100 move (e.g., rotate) together, as indicated by arrows "U" (FIG. 9A), for example, to derotate the spinal column.

In use, and with reference to FIGS. 1, 2, and FIGS. 6-10B, the derotation sleeve 320 of the rod reducer assembly 300 is mounted over the pedicle screw assembly 100 and advanced distally along the pedicle screw assembly 100 until the fingers 322a, 322b of upper shaft portion 322 of the derotation sleeve 320 engage (e.g., "snap" into) or lock into the grooves 160a, 160b of the extension assembly 140 of the pedicle screw assembly 100 (FIG. 8B). Initially, the locking mechanism 330 is disposed in the unlocked position with the teeth 331 of upper shaft portion 322 of the derotation sleeve 320 disengaged and spaced from the recesses 332 of the lower shaft portion 323 by the gap "G".

In order to position the locking mechanism 330 of the derotation sleeve 320 into the locked position, a rotational (e.g., clockwise and/or counterclockwise) force is applied to the knob 321 of the derotation sleeve 320, as indicated by arrow "X," (FIG. 6) so that the threads 321b of the knob 321 engage with the threads 322c of the upper shaft portion 322 of the derotation sleeve 320. As the knob 321 rotates, the threaded engagement between the knob 321 and the upper shaft portion 322 moves the knob 321 distally along the threads 322c of the upper shaft portion 322, as indicated by arrow "W" (see FIGS. 6 and 8B). The distal movement of the knob 321 relative to the upper shaft portion 322 causes the first portion 3210 of the upper shaft portion 322 to move distally until the teeth 331 (FIG. 7B) of the locking mechanism 330 engage with the recesses 332 of the locking mechanism 330 (FIG. 9B). Once the teeth 331 are fully seated within the recesses 332, the locking mechanism 330 is disposed in the locked position such that the upper and lower shaft portions 322, 324 are locked together with the gap "G" (FIG. 8B) eliminated or substantially reduced as seen in at least FIGS. 9A, 9B, 10A, and 10B.

With the locking mechanism 330 of the derotation sleeve 330 disposed in the locked position on the pedicle screw assembly 100, the derotation sleeve 320 and the pedicle screw assembly 100 can move together to manipulate the spine as desired, for example, to derotate the spine and/or to correct a spinal deformity. More particularly, the derotation sleeve 330 is positioned on the pedicle screw assembly 100 so that the frangible members 132b, 134b, 156a, 156b of the pedicle screw assembly 100 are stabilized to inhibit the frangible members 132b, 134b, 156a, 156b from breaking during derotation of the spine. For a more detailed description of related spinal derotation devices and methods, reference can be made, for example, to U.S. Pat. No. 8,956,360, the entire contents of which are incorporated by reference herein. Reference can also be made to International Application No. PCT/US16/46523, the entire contents of which are also incorporated by reference herein.

When a clinician desires to reduce a spinal rod "R" into the pedicle screw assembly 100, the clinician can insert the spinal rod "R" between the first and second legs 324a, 324b of derotation sleeve 320 and the extensions 142, 144 (FIG. 1) of the extension assembly 140 of the pedicle screw assembly 100. The rod reducer 310 may be mounted to the derotation sleeve 320 while the derotation sleeve 320 is mounted on the pedicle screw assembly 100 to reduce the spinal rod "R" into the saddle 128b (FIG. 2) of the pedicle screw assembly 100.

As seen in FIGS. 5, 11A, 11B, 12A, and 12B, the rod reducer 310 of the rod reducer assembly 300 includes a cap 310a that is rotatably coupled to a sleeve assembly 310b, as indicated by arrows "Q" (FIG. 11A), by a retaining ring 310c. The cap 310a of the rod reducer 310 includes a distal portion with a threaded outer surface 311a and a proximal gripping portion 311b.

Figure 11A:
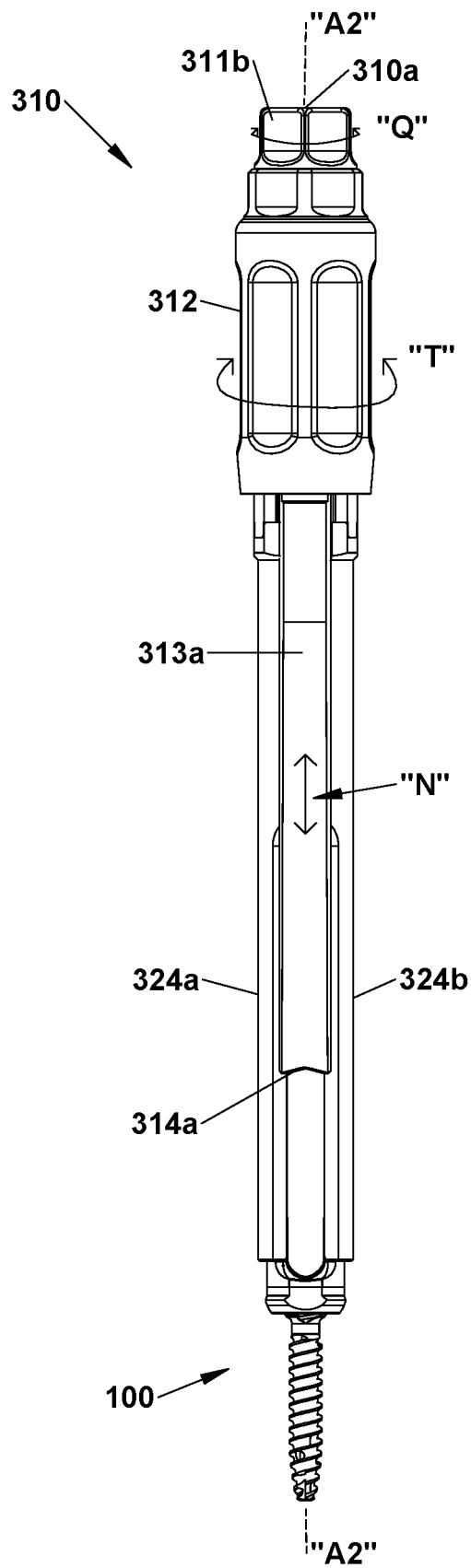
FIG. 11A is a front view of the rod reducer assembly of FIG. 5 with a rod reducer of the rod reducer assembly shown in an unreduced position.
Figure 12A:
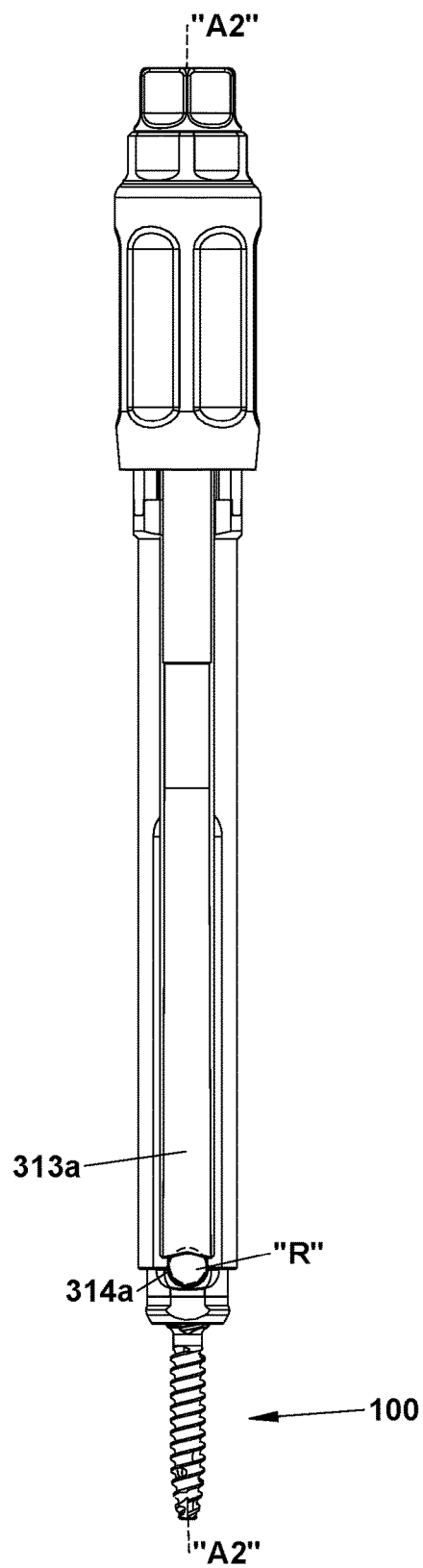
FIG. 12A is a front view of the rod reducer assembly of FIG. 5 shown in a reduced position.
Figure 12B:
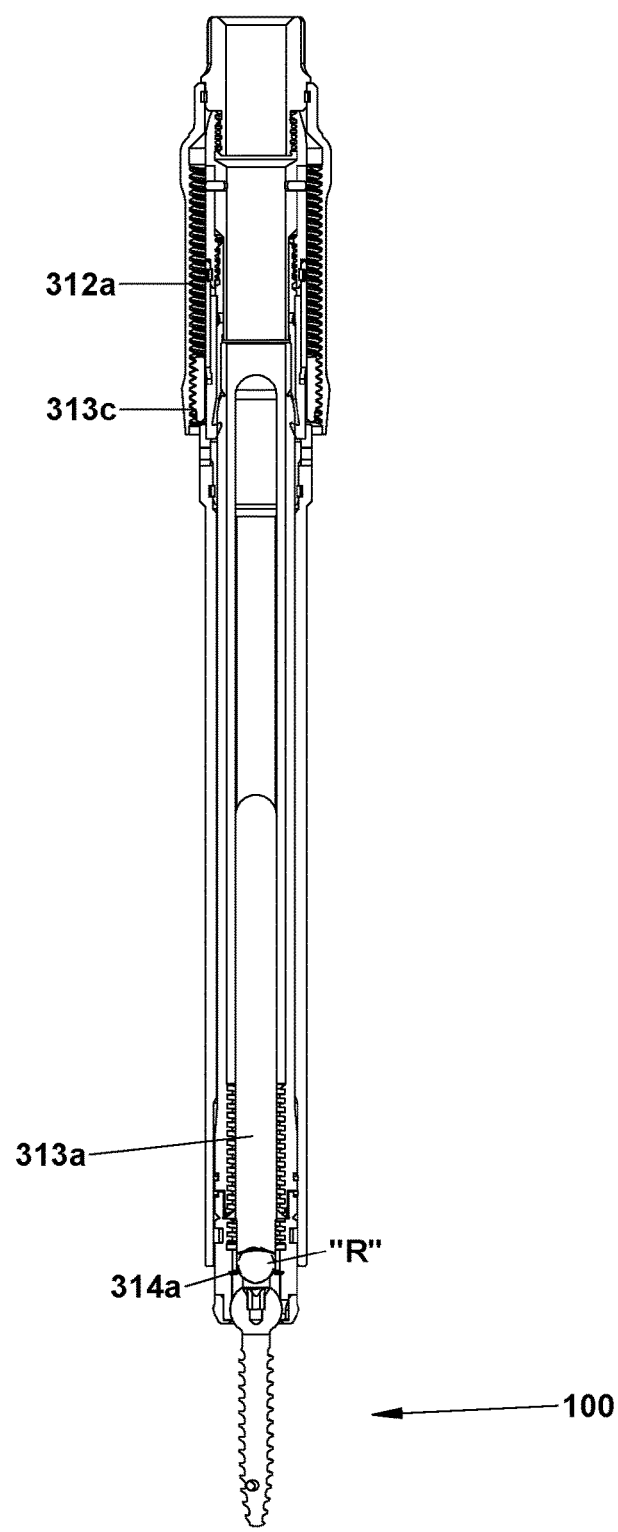
FIG. 12B is a longitudinal, cross-sectional view of the rod reducer assembly of FIG. 5, as depicted in FIG. 12A.
Figure 13:
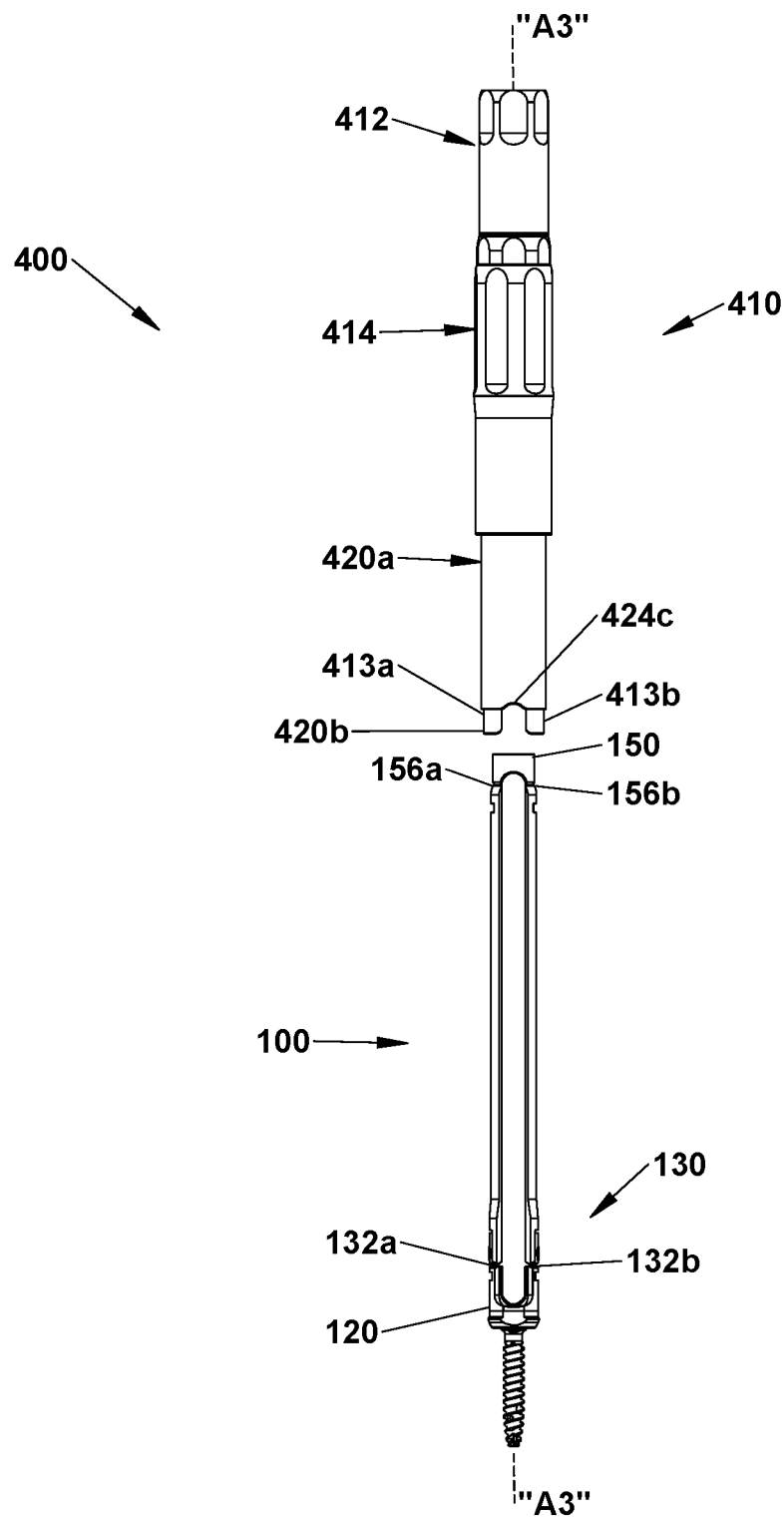
FIG. 13 is a front view, with parts separated, of another embodiment of a rod reducer assembly in accordance with the present disclosure.
Figure 14:
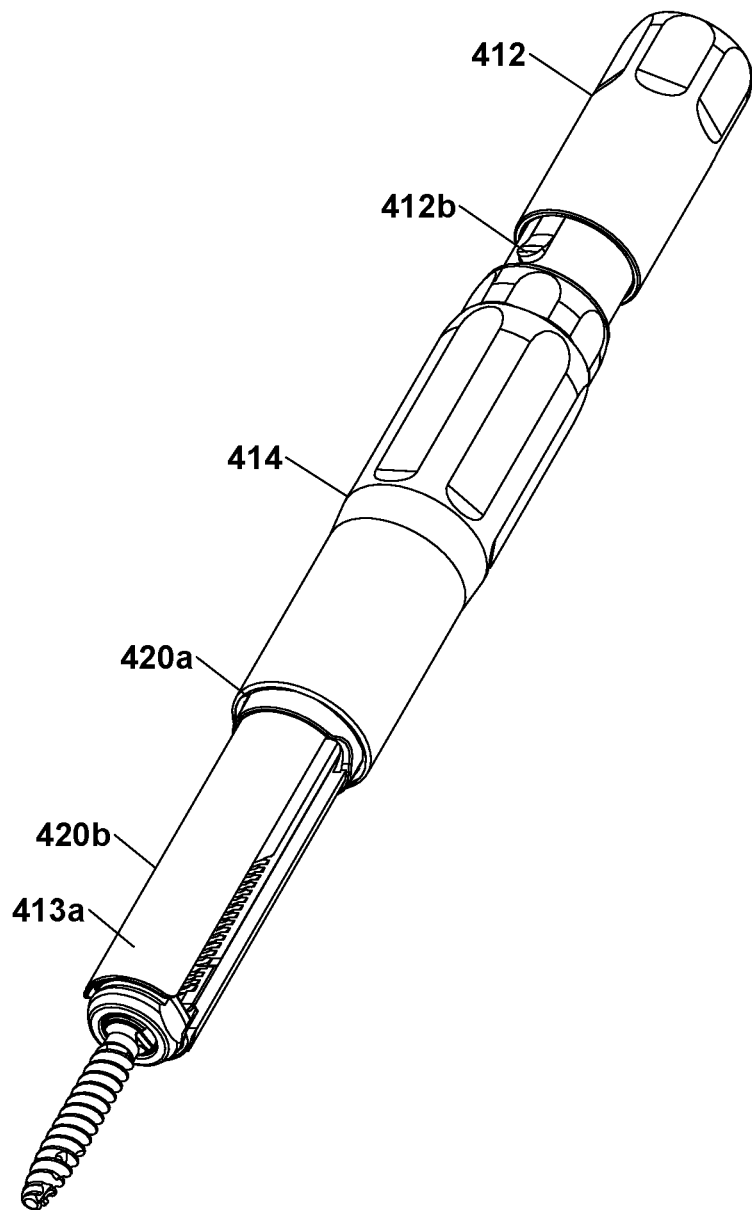
FIG. 14 is a perspective view of the rod reducer assembly of FIG. 13 with a knob thereof shown unapproximated from a central shaft thereof.

The sleeve assembly 310b includes an outer sleeve 312 that is rotatably coupled to an inner sleeve 313, as indicated by arrow "T" (FIG. 11A), to enable the inner sleeve 313 to advance axially relative to the outer sleeve 312, as indicated by arrow "N," between a proximal or unreduced position (FIG. 11A) and a distal or reduced position (FIG. 12A). The outer sleeve 312 includes an internal threaded surface 312a. The inner sleeve 313 includes a first arm 313a and a second arm 313b that are coupled by a nut 313c having an inner surface 313d and a threaded outer surface 313e. The threaded outer surface 313e of the nut 313c is threadably engagable with internal threaded surface 312a of the outer sleeve 312 to enable the outer sleeve 312 to rotate about the longitudinal axis "A2-A2" of the rod reducer assembly 300 and relative to the inner sleeve 313 thereof. The first and second arms 313a, 313b of the inner sleeve 313 extend distally from opposite sides of the nut 313c to rod-engaging recesses 314a, 314b, respectively. The rod-engaging recesses 314a, 314b of the inner sleeve 313 may include inverted U-shaped or arched configurations.

Figure 11B:
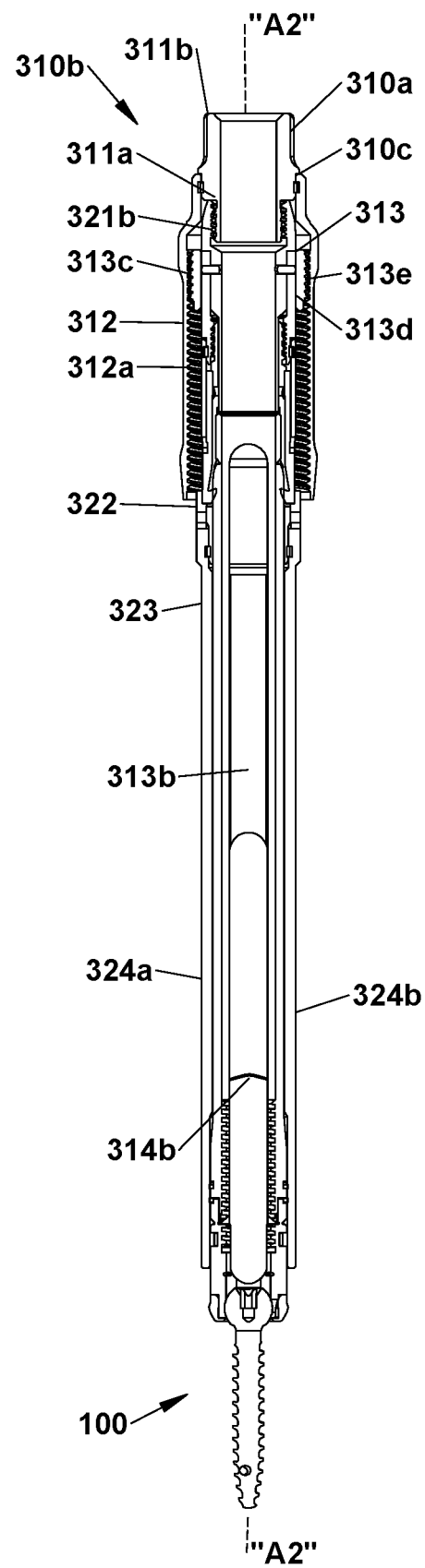
FIG. 11B is a longitudinal, cross-sectional view of the rod reducer assembly of FIG. 5, as depicted in FIG. 11A.

In use, the rod reducer 310 of the rod reducer assembly 300 is mounted over the derotation sleeve 320 so that the distal portion of the cap 310a of the rod reducer 310 is threadably received in the proximal end of the knob 321 of the derotation sleeve 320 as seen in FIGS. 11A and 11B. Specifically, the threaded outer surface 311a of the cap 310a of the rod reducer 310 threadably engages with the internal threaded surface 321a of the knob 321 of the derotation sleeve 320 to mount the rod reducer 310 to the derotation sleeve 320 and the pedicle screw assembly 100.

Once the rod reducer 310 is threadably mounted onto the derotation sleeve 320, the outer sleeve 312 of the rod reducer 310 can be rotated relative to the inner sleeve 313, as indicated by arrows "T," to drive the first and second arms 313a, 313b of the inner sleeve 313 distally from the unreduced position (FIGS. 11A and 11B) to the reduced position (FIGS. 12A and 12B) and reduce the spinal rod "R" into the saddle 128b (FIG. 2) of the pedicle screw assembly 100.

With the frangible members 132b, 134b, 156a, 156b of the pedicle screw assembly 100 (see FIGS. 1 and 2) supported/stabilized by the derotation sleeve 320, the entire rod reducer assembly 300 can likewise be manipulated to selectively position and/or reposition the rod reducer assembly 300, the spinal column, and/or portions of the spinal column as desired. It should be appreciated that derotation of the spine and compression and distraction of vertebrae may be performed with, or without, the rod reducer 310 mounted to the derotation sleeve 320.

The rod reducer 310 may be removed from the derotation sleeve 320 by unthreading of the cap 310a from the knob 321 of the derotation sleeve 320. The derotation sleeve 320 may be removed by unthreading the knob 321 of the derotation sleeve 320 from the upper shaft portion 322 of the derotation sleeve 320 so that the teeth 331 of to the locking mechanism 330 of the derotation sleeve 320 disengage from the recesses 332 of the locking mechanism 330 to unlock the locking mechanism 330 and separate and upper and lower shaft portions 322, 323. With the locking mechanism 330 unlocked, the upper shaft portion 322 can be rotated relative to the lower shaft portion 323 so that the fingers 322a, 322b of the upper shaft portion 322 rotatably cam out of the grooves 160a, 160b of the extension assembly 140 and the derotation sleeve 320 separates from the pedicle screw assembly 100.

Referring now to FIGS. 1, 2, 13 and 14, a rod reducer assembly in accordance with another embodiment of the present disclosure is shown and generally designated as 400. The rod reducer assembly 400 is positionable on the pedicle screw assembly 100 and configured to reduce the spinal rod "R" (FIG. 2) into the pedicle screw housing 120 of the pedicle screw assembly 100 and to inhibit the frangible members 132b, 134b, 156a, 156b of the tab and head assemblies 130, 150 of the pedicle screw assembly 100, respectively, from prematurely breaking during a derotation and/or manipulation of the spine.

By virtue of the structural arrangement of one or more of the components of the rod reducer assembly 400 and/or the rigidity thereof, the rod reducer assembly 400 is configured to reinforce the pedicle screw assembly 100, extension assembly 140, the tab assembly 130, and/or the head assembly 150 by limiting forces (e.g., twisting, bending, flexing, tensile, and/or shear forces) from being applied (e.g. directly) to the frangible members 132b, 134b of the pedicle screw assembly 100 and/or to the frangible members 156a, 156b of the head assembly 150 (e.g., in one or more caudad, cephalad, posterior, anterior, and/or lateral directions). Instead, the rod reducer assembly 400 and/or components thereof, are configured to absorb these forces and inhibit the tabs 132, 134 of the tab assembly 130 from prematurely separating from the flanges 122a, 122b of the pedicle screw housing 120 and/or the head assembly 150 from prematurely separating from the extension assembly 140.

With reference also to FIGS. 15A, 15B, 16, and 18, the rod reducer assembly 400 defines a longitudinal axis "A3-A3" and generally includes the pedicle screw assembly 100 and a rod reducer 410. The rod reducer 410 includes a knob assembly 412 configured to selectively mount the rod reducer 410 to the pedicle screw assembly 100 and a reduction sleeve assembly 414 coupled to the knob assembly 412 and configured to reduce the spinal rod "R" (FIG. 2) into the pedicle screw assembly 100 while the rod reducer 410 is mounted to the pedicle screw assembly 100.

The knob assembly 412 of the rod reducer 410 includes an outer sleeve 412a that defines a threaded internal surface 412b and an inner sleeve 412c. The outer sleeve 412a is rotatable (e.g., clockwise and/or counterclockwise) about the inner sleeve 412c, as indicated by arrows "H," and axially movable along the longitudinal axis "A3-A3" between a proximal position (FIG. 15A) and distal position (FIG. 16), as indicated by arrows "I." The inner sleeve 412c is positioned within the outer sleeve 412a and includes a proximal portion 412d, a central portion 412e, and a distal portion 412f. The proximal portion 412d of the inner sleeve 412c includes a threaded outer surface 412g that threadably engages the threaded internal surface 412b of the outer sleeve 412a. The central portion 412e of the inner sleeve 412c includes first and second fingers 412h, 412i supported on opposite sides of the central portion 412e. The first and second fingers 412h, 412i, which may each be in the form of a hook, are biased radially outward and are configured to be received within the grooves 160a and 160b of the pedicle screw assembly 100. The distal portion 412f of the inner sleeve 412c is received within a proximal portion of the reduction sleeve assembly 414 and coupled to the reduction sleeve assembly 414 by a retaining ring 416.

Figure 18:
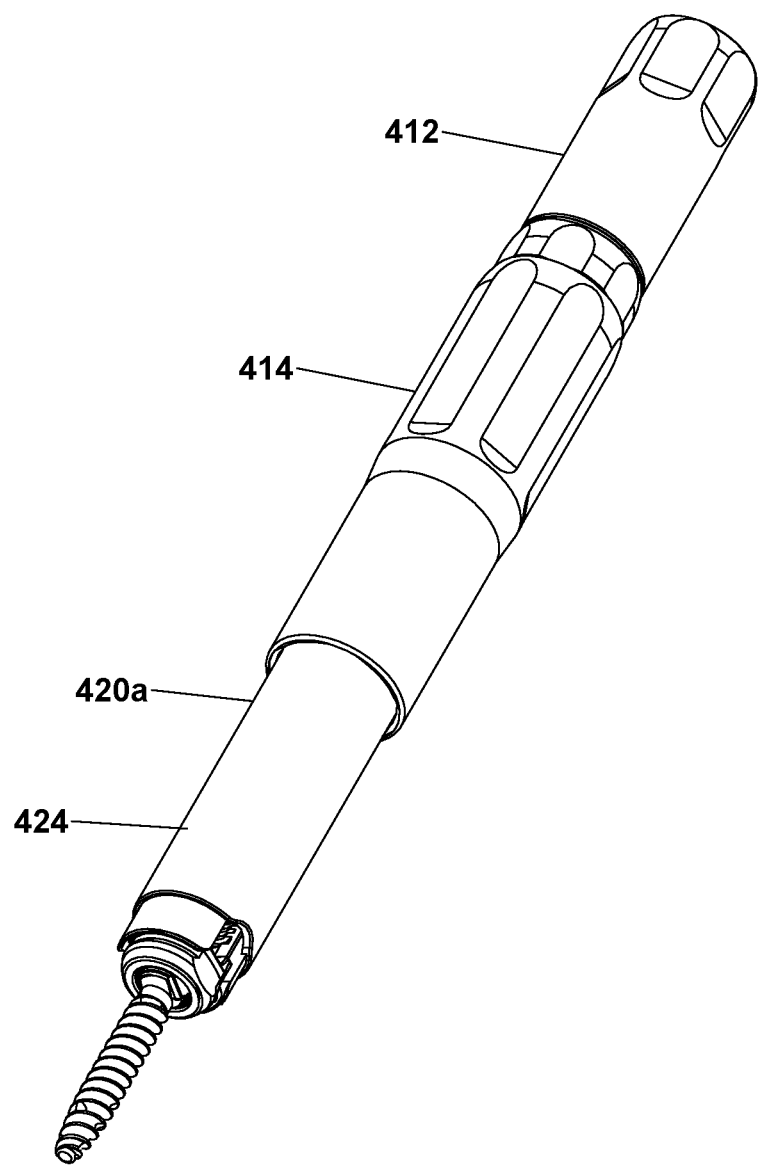
FIG. 18 is a perspective view of the rod reducer assembly of FIG. 13 shown in a locked and reduced position.

The reduction sleeve assembly 414 of the rod reducer assembly 400 includes an outer sleeve 418, a first inner sleeve 420a coupled to the outer sleeve 418 and configured to reduce the spinal rod "R" in response to rotation of the outer sleeve 418, and a second inner sleeve 420b coupled to the first inner sleeve 420a and configured to mount to the pedicle screw housing 120 of the pedicle screw assembly 100. The first and second inner sleeves 420a, 420b are positioned within the outer sleeve 418. As indicated by arrow "F" (FIG. 15A), the outer sleeve 418 is rotatable about the longitudinal axis "A3-A3" relative to the inner sleeves 420a, 420b. As seen in FIG. 18, and as indicated by arrows "O," the first inner sleeve 420a is axially movable along the longitudinal axis "A3-A3" of the rod reducer assembly 400 relative to the outer sleeve 418 and the second inner sleeve 420b between a proximal or unreduced position (FIG. 16) and a distal or reduced position (FIG. 18). The outer sleeve 418 of the reduction sleeve assembly 414 is rotatably coupled to the distal portion 412f of the inner sleeve 412c of the knob assembly 412 by the retaining ring 416. The retaining ring 416 is configured to enable the outer sleeve 418 of the reduction sleeve assembly 414 to rotate relative to the inner sleeve 412c of the knob assembly 412 and the first and second inner sleeves 420a, 420b of the reduction sleeve assembly 414. The outer sleeve 418 includes an outer surface 418a and a threaded inner surface 418b.

Figure 19A:
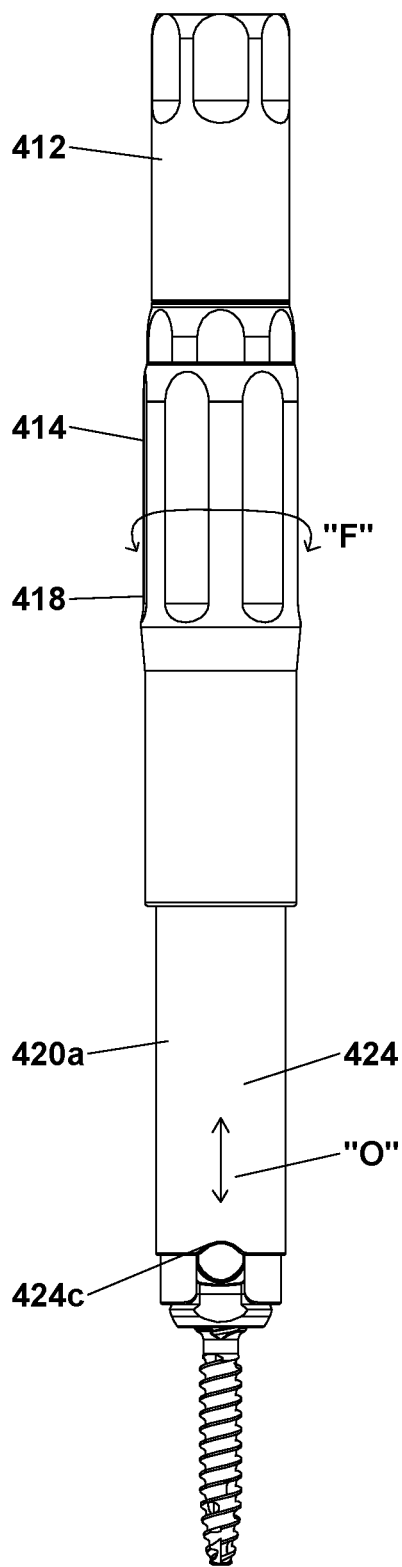
FIG. 19A is a front view of the rod reducer assembly of FIG. 13, as depicted in FIG. 18.
Figure 19B:
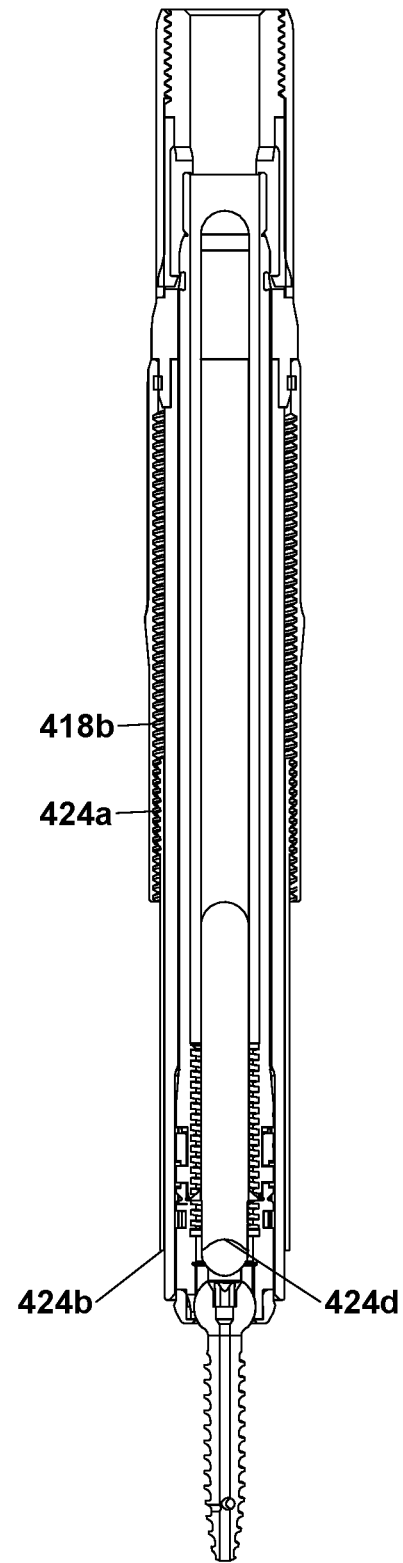
FIG. 19B is a longitudinal, cross-sectional view of the rod reducer assembly of FIG. 13, as depicted in FIG. 19A.

The first inner sleeve 420a of the reduction sleeve assembly 414 is axially advanceable along the pedicle screw assembly 100. The first inner sleeve 420a has a tubular body 424 having a threaded proximal end portion 424a and a distal end portion 424b. The distal end portion 424b (FIG. 19B) of the first inner sleeve 420a defines a first rod-engaging recess 424c on a first side of the tubular body 424 and a second rod-engaging recess 424d on a second side of the tubular body 424. The first and second recesses 424c, 424d are positioned to engage the spinal rod "R" and may have an inverted U-shaped or arched configuration.

The second inner sleeve 420b has a tubular proximal portion fixedly supported within the inner sleeve 412c of the knob assembly 412 and a distal portion having first and second legs 413a, 413b that are configured to couple to outer side surfaces of the pedicle screw housing 120 of the pedicle screw assembly 100 to support the rod reducer 410 on the pedicle screw assembly 100. The first and second legs 413a, 413b define a spinal rod passage 413c configured to slidably receive a spinal rod "R" (FIG. 2) axially therealong.

With reference to FIGS. 13-19B, in use, the rod reducer 410 is mounted over the pedicle screw assembly 100 with the outer sleeve 412a of the knob assembly 412 of the rod reducer 410 in the proximal position and the first and second fingers 412h, 412i of the knob assembly 412 biased radially outward and axially aligned with the grooves 160a and 160b of the pedicle screw assembly 100. In order to secure the rod reducer 410 to the pedicle screw assembly 100, the outer sleeve 412a of the knob assembly 412 is rotated relative to the inner sleeve 412c of the knob assembly 412 until the outer sleeve 412a engages the first and second fingers 412h, 412i of the inner sleeve 412c of the knob assembly 412. As the outer sleeve 412a continues to advance distally toward the distal position of the inner sleeve 412c, the outer sleeve 412a urges the fingers 412h, 412i of the inner sleeve 412c radially inward into the grooves 160a and 160b of the pedicle screw assembly 100, as indicated by arrows "E" (FIG. 17B). With the fingers 412h, 412i of the inner sleeve 412c positioned in the grooves 160a and 160b of the pedicle screw assembly 100, the rod reducer 410 is locked onto the pedicle screw assembly 100.

Once the rod reducer 410 of the rod reducer assembly 400 is locked onto the pedicle screw assembly 100 of the rod reducer assembly 400, the rod reducer 410 may be used to manipulate and/or derotate the spine or correct a spinal deformity while supporting/stabilizing the frangible members 132b, 134b, 156a, 156b of the pedicle screw assembly 100. While locked onto the pedicle screw assembly 100, the rod reducer 410 is configured to inhibit the frangible members 132b, 134b, 156a, 156b of the pedicle screw assembly 100 from prematurely breaking during a derotation and/or manipulation procedure.

Figure 15A:
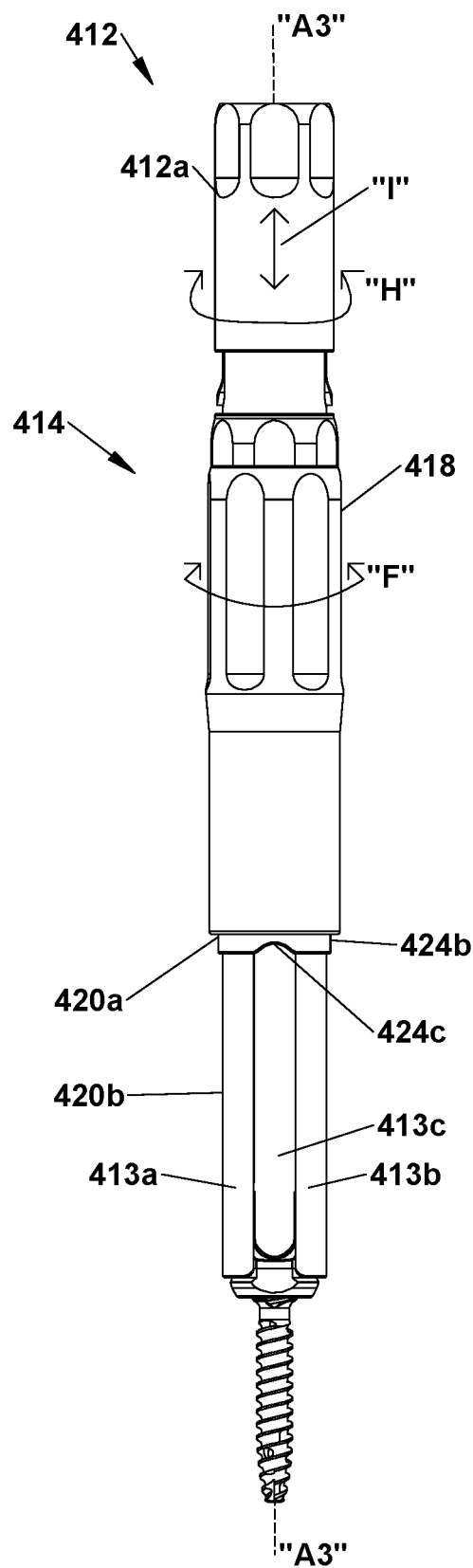
FIG. 15A is a front view of the rod reducer assembly of FIG. 13, as depicted in FIG. 14, with the rod reducer assembly shown supporting a spinal rod and in an unlocked and unreduced position.
Figure 15B:
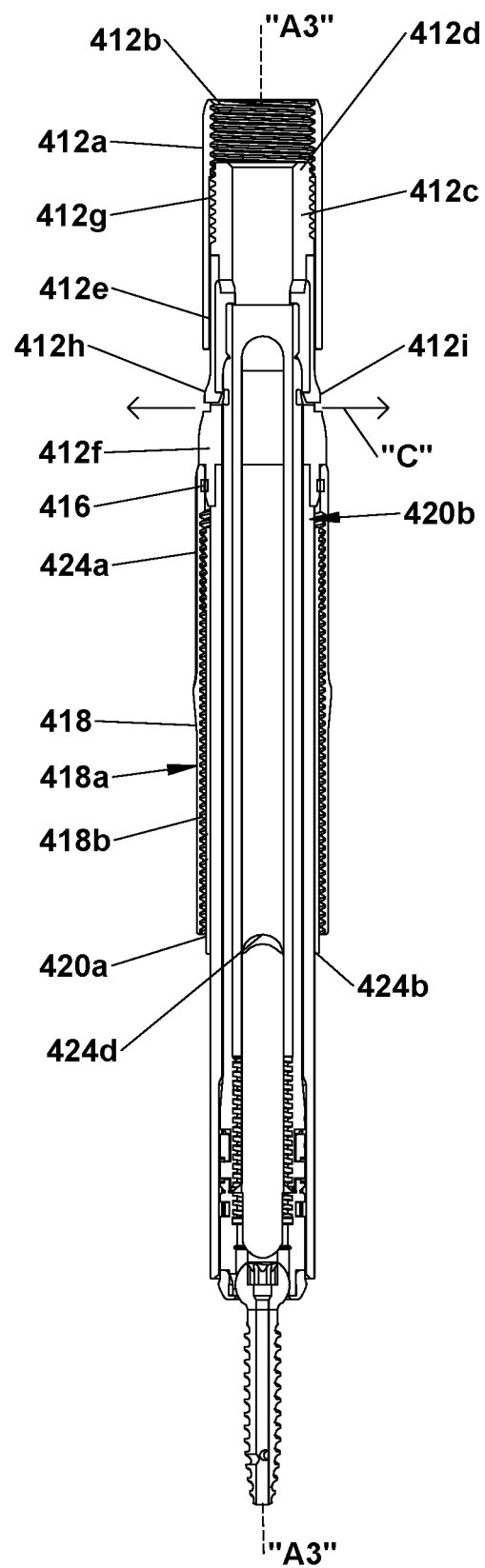
FIG. 15B is a longitudinal, cross-sectional view of the rod reducer assembly of FIG. 13, as depicted in FIG. 15A.
Figure 16:
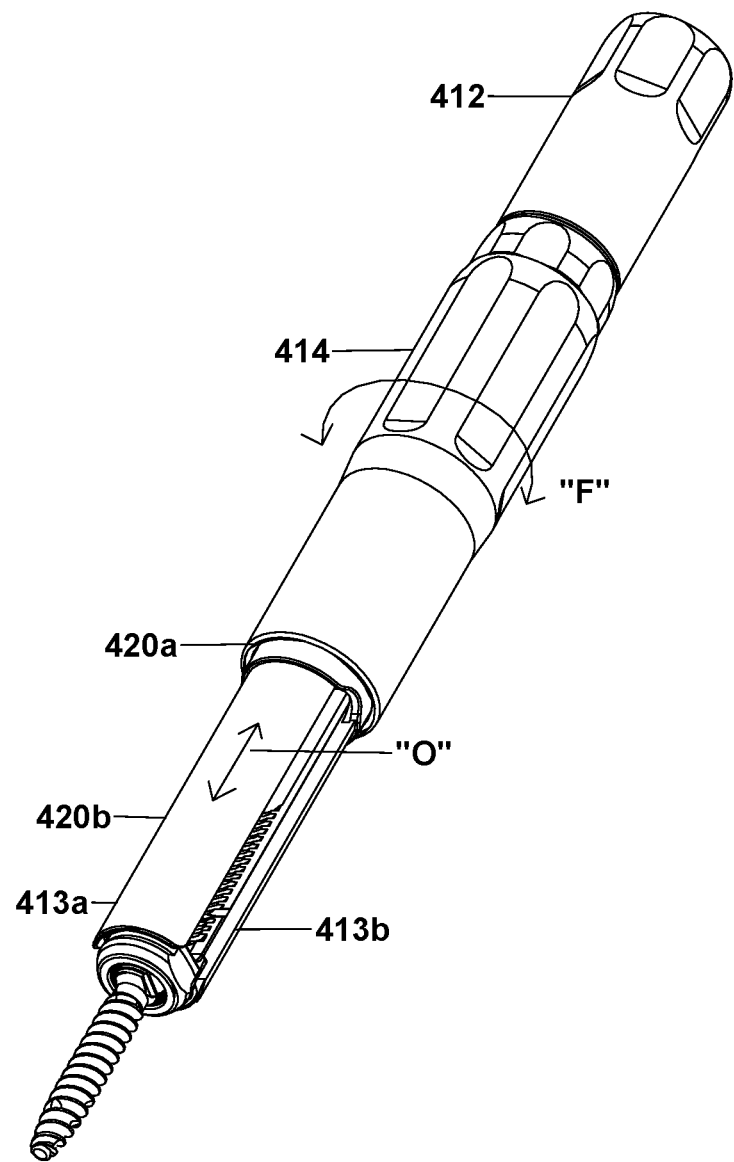
FIG. 16 is a perspective view of the rod reducer assembly of FIG. 13 shown in a locked position with the knob and central shaft thereof approximated with one another.

In order to reduce the spinal rod "R" (FIG. 2) into the pedicle screw housing 120 of the pedicle screw assembly 100, the outer sleeve 418 of the reduction sleeve assembly 414 of the rod reducer assembly 400 is rotated relative to the inner sleeves 420a, 420b of the reduction sleeve assembly 414, as indicated by arrows "F" (FIG. 15A). As the outer sleeve 418 is rotated, the first inner sleeve 420a moves distally relative to the second inner sleeve 420b and along the pedicle screw assembly 100 by virtue of the threaded engagement between the first inner sleeve 420a and the outer sleeve 418. Distal advancement of the first inner sleeve 420a causes the first and second recesses 424c, 424d to engage and reduce the spinal rod "R" into the pedicle screw housing 120 of the pedicle screw assembly 100. To remove the rod reducer 410 of the rod reducer assembly 400 from the pedicle screw assembly 100 of the rod reducer assembly 400, the outer sleeve 412a of the knob assembly 412 is rotated to advance the outer sleeve 412a of the knob assembly 412 proximally relative to the inner sleeve 412c of the knob assembly 412 until the fingers 412h, 412i of the inner sleeve 412c are exposed. With the fingers 412h, 412i exposed, the fingers 412h, 412i are configured to bias radially outward from within the grooves 160a and 160b of the pedicle screw assembly 100, as indicated by arrows "C" (FIG. 15B). The rod reducer 410 may then be removed from the pedicle screw assembly 100.

With any of the presently disclosed rod reducers coupled or uncoupled to the presently disclosed pedicle screw assemblies, a set screw "S" (FIG. 20B) may be threaded into the pedicle screw housing 120 of the pedicle screw assembly 100 via the threaded internal surface 124a of the pedicle screw housing 120 to facilitate seating and/or securement of the spinal rod "R" into the saddle 128b of the pedicle screw housing 120.

Referring now to FIG. 20A, a surgical system for mounting and/or manipulating spinal rods "R" and/or pedicle screw assemblies to a spinal column is provided. The surgical system is generally designated as 500. The surgical system 500 may be used to manipulate vertebrae in conjunction with any of the presently disclosed rod reducer assemblies. The surgical system 500 includes a handle 510 selectively attachable to one or more drivers 520 for mounting one or more pedicle screw assemblies 100 to a spine and/or for securing one or more set screws "S" to the one or more pedicle screw assemblies 100. The surgical system 500 further includes a fulcrum 530 mountable to the one or more drivers 520 for supporting the drivers 520 and a distraction and compression instrument 540 selectively engagable with the one or more drivers 520 to approximate or unapproximate the one or more drivers 520.

The handle 510 of the surgical system 500 includes a gripping portion 511 at a proximal end thereof and a mounting sleeve 512 at a distal end thereof for mounting to a proximal end of the driver 520. The driver 520 includes an elongated shaft 520b and a driving bit 521 that extends distally from the elongated shaft 520b. The driver 520 further includes a boss 522 disposed along elongated shaft 520b.

The fulcrum 530 of the surgical system 500 includes a body 531 defining apertures 531a. Each of the apertures 531a is configured to receive the boss 522 of one of the drivers 520 such that adjacent drivers 520 can be positioned adjacent one another.

Figure 21:
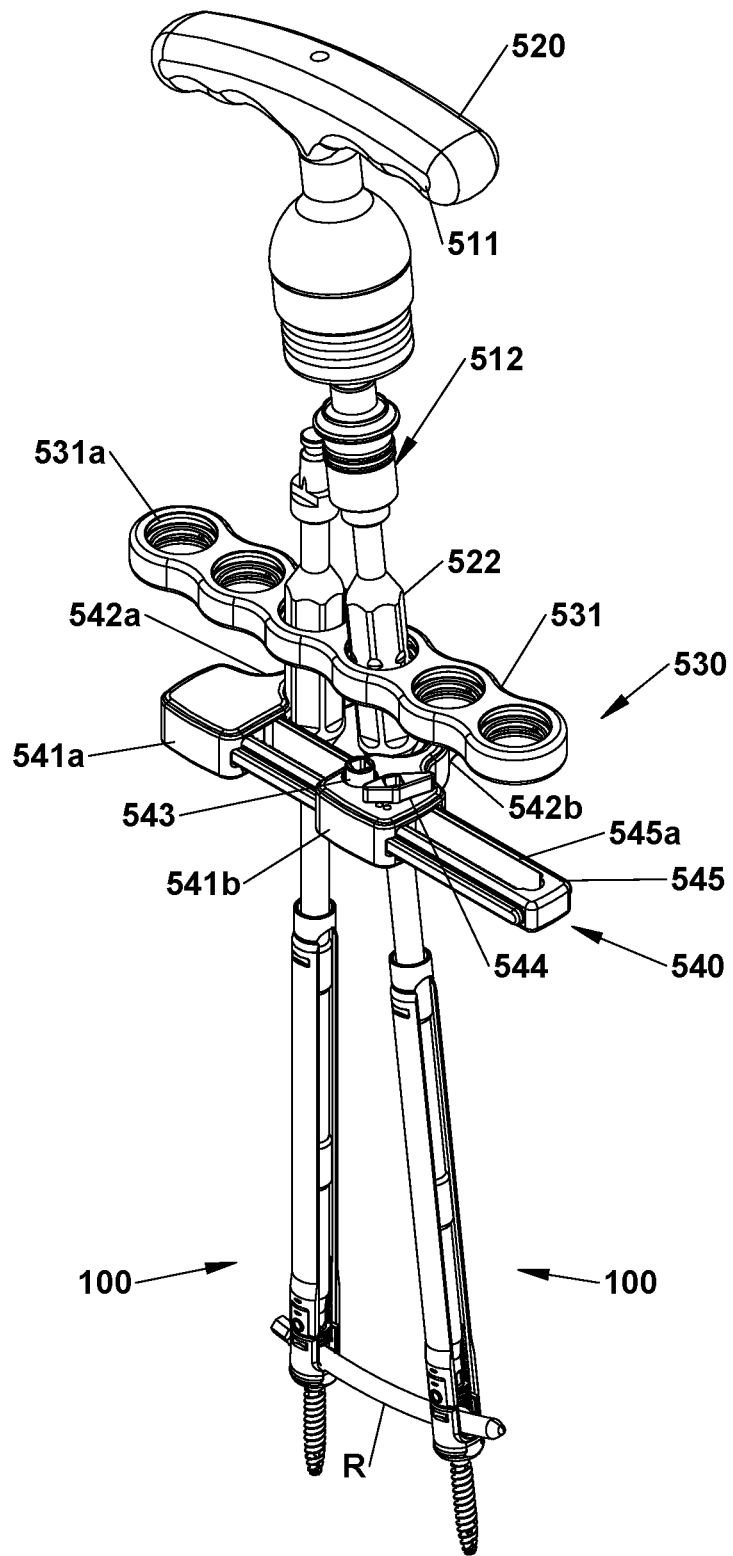
FIG. 21 is a perspective view of the surgical system of FIG. 20A with the distraction and compression instrument shown coupled to the surgical system in a compression mode.

The distraction and compression instrument 540 of the surgical system 500 includes a stationary body 541a having a wing 542a extending therefrom, and a movable body 541b having a wing 542b extending therefrom. The stationary and movable body 541a, 541b are supported on a dial 545 having teeth 545a for slidably engaging with movable body 541b as the movable body 541b moves along the dial 545, as indicated by arrows "B," (FIG. 20A) relative to the stationary body 541a between approximated (FIG. 20A) and unapproximated positions (FIG. 21). The movable body 541b includes a driver receiver 543 that is operatively coupled to the teeth 545a of the dial 545 and is rotatable, as indicated by arrows "M" (FIG. 20A), to slide the movable body 541b along the dial 545 between the approximated and unapproximated positions relative to the stationary body 541a. The movable body 541b further includes a switch 544 that is operable to select between a distraction mode, in which the movable body 541b moves away or unapproximates from the stationary body 541a as the driver receiver 543 rotates, and a compression mode, in which the movable body 541b moves toward or approximates the stationary body 541b as the driver receiver 543 rotates.

In use, once one or more pedicle screw assemblies 100 are installed into adjacent vertebrae, and a spinal rod "R" is reduced into the pedicle screw housings 120 thereof, one or more drivers 520 may be introduced into the pedicle screw assemblies 100 to tighten a set screw "S" against the spinal rod "R" to facilitate seating of the spinal rod "R," for example. The fulcrum 530 can be mounted to the bosses 522 of each driver 520 to support the drivers 520 relative to one another. The distraction and compression instrument 540 can be coupled to adjacent drivers 520 with the wings 542a, 542b of the stationary and movable bodies 541a, 541b, respectively, positioned in contact with the adjacent drivers 520. The driver receiver 543 can then be rotated to move the movable body 541b relative to the stationary body 541a of the distraction and compression instrument 540. Depending on whether the switch 544 is in the compression or distraction mode, the wings 542a, 542b of the stationary and movable bodies 541a, 541b, respectively, will either compress or distract the drivers 520 relative to one another as desired to cause a corresponding separation and/or distraction of one or more vertebrae of the spinal column to which the surgical system 500 is attached. When the spinal column, or portion thereof are in a desired position, one or more set screw "S" can be tightened as necessary to secure or fix the position of one or more of the spinal rods "R" and/or one or more of the pedicle screw assemblies 100.

One or more of the components of the surgical system 500 can then be removed from the pedicle screw assemblies 100 and the frangible members 132b, 134b, 156a, and 156b (FIG. 2) thereof can be broken to remove, for example, the extension assemblies 140 of the pedicle screw assemblies 100 from the respective pedicle screw housings 120 (with the one or more spinal rods "R" secured thereto for maintaining the spine in a corrected position) as described herein or as detailed in International Application No. PCT/US16/46523 incorporated herein by reference.

Figure 22:
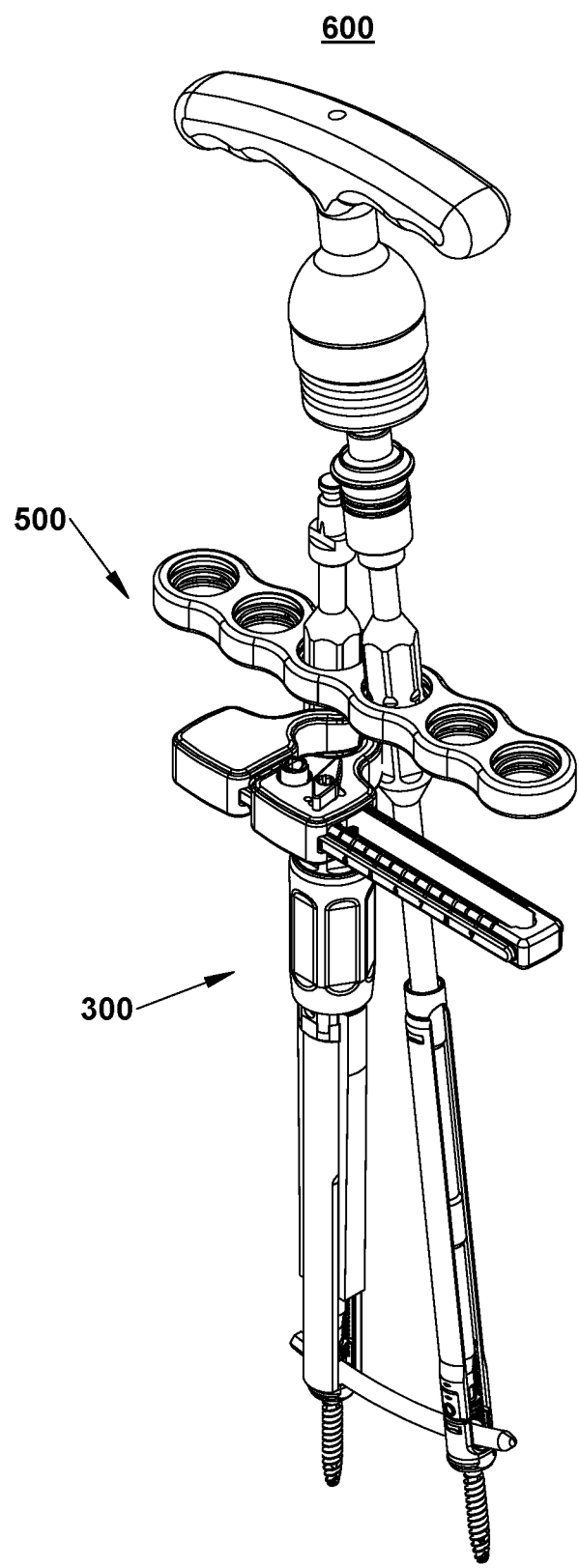
FIG. 22 is a perspective view of another embodiment of a surgical system in accordance with the present disclosure.
Figures 23A, 23B:
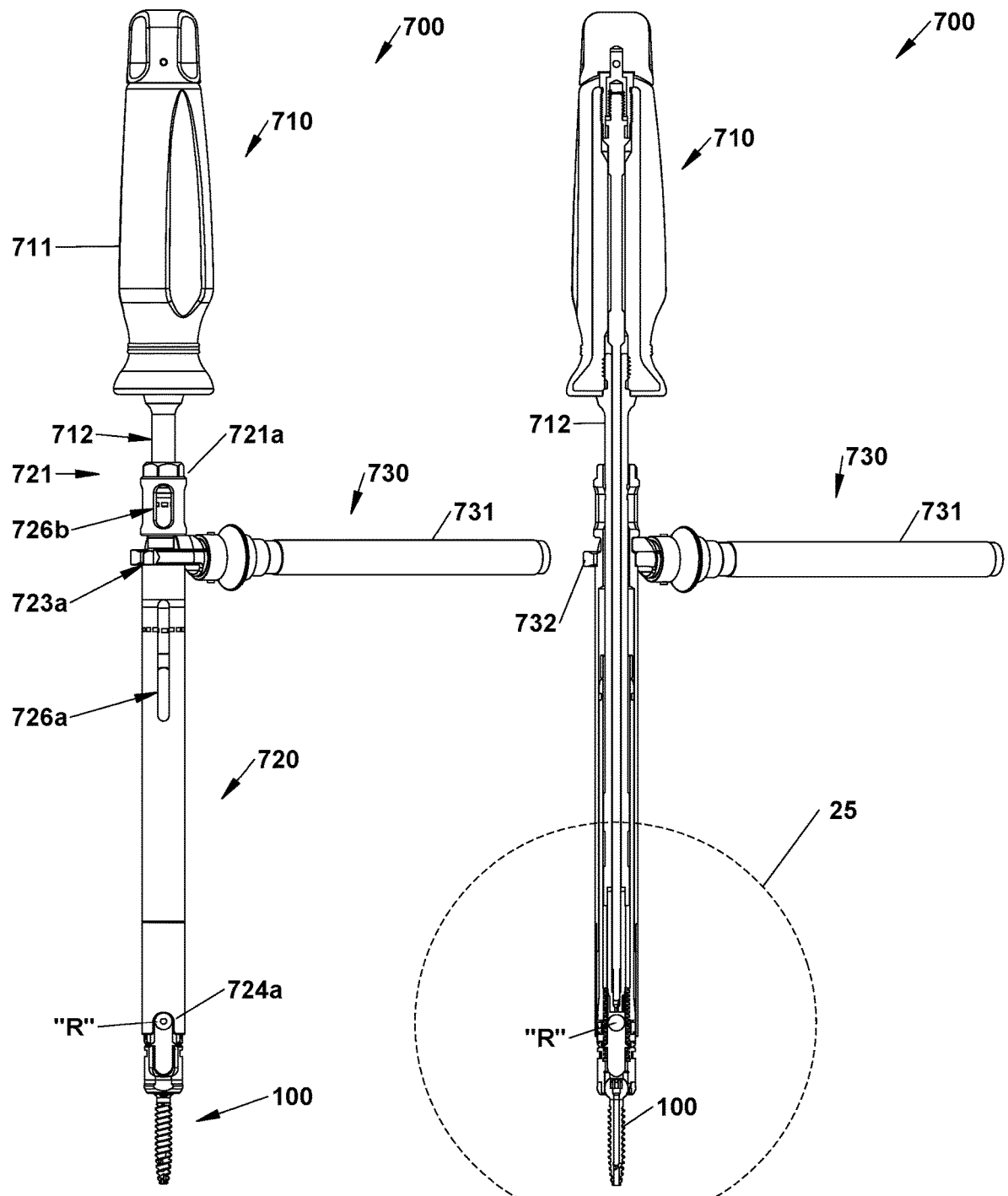
FIG. 23A is a front view of a surgical system in accordance with another embodiment of the present disclosure.
FIG. 23B is a longitudinal, cross-sectional view of the surgical system of FIG. 23A.
Figure 25:
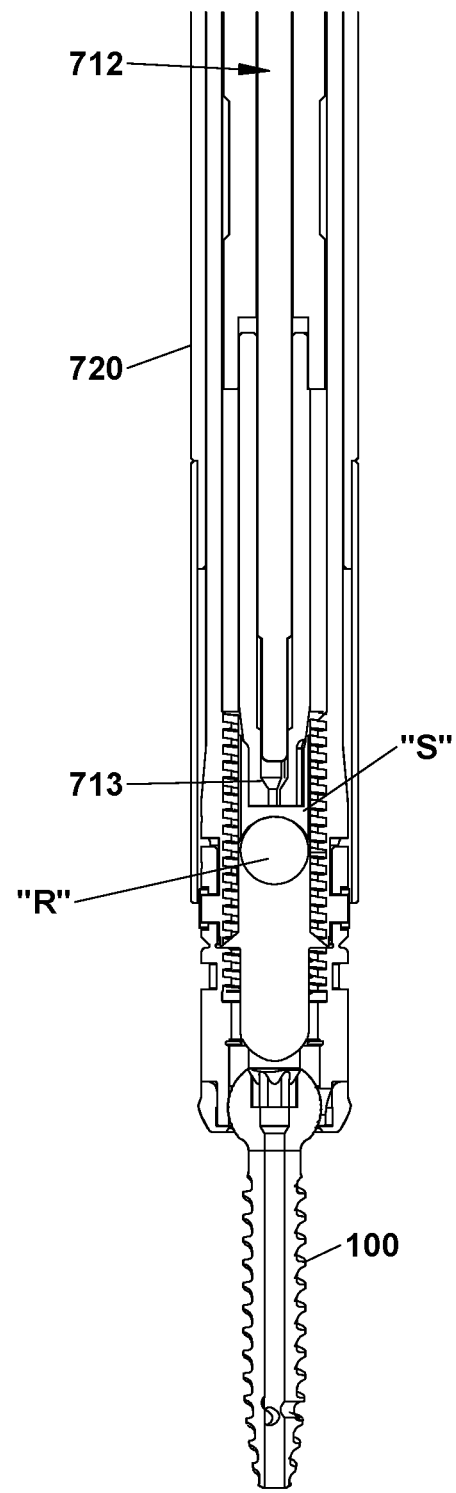
FIG. 25 is an enlarged, longitudinal, cross-sectional view of the indicated area of detail delineated in FIG. 23B.

With reference to FIG. 22, a surgical system in accordance with another embodiment of the present disclosure is shown and generally designated as 600 may include, or be used with, any of the presently disclosed rod reducing assemblies.

With reference to FIGS. 23A, 23B, 24A, 24B, 25, and 26, a surgical system in accordance with another embodiment of the present disclosure is shown and generally designated 700. The surgical system 700 may be used to manipulate the spine while inhibiting the frangible members 132b, 134b and 156a, 156b of the tab and head assemblies 130, 150 of the pedicle screw assembly 100, respectively, from breaking as the set screw "S" is driven into the pedicle screw housing 120 of the pedicle screw assembly 100.

The surgical system 700 generally includes a pedicle screw assembly 100, a driver 710, a support sleeve 720, and an anti-torque tool 730. The driver 710 is used for rotating the set screw "S" into the pedicle screw housing 120 (FIG. 1) of the pedicle screw assembly 100. The support sleeve 720 is selectively mountable to the pedicle screw assembly 100 and is configured to support the pedicle screw assembly 100 as the set screw "S" is reduced into the pedicle screw assembly 100. The anti-torque tool 730 is configured to selectively attach to the support sleeve 720 to inhibit unwanted rotation of the pedicle screw assembly 100 and the support sleeve 720, for example, as the driver 710 rotates the set screw "S" into the pedicle screw assembly 100.

The driver 710 of the surgical system 700 includes a handle 711 for gripping the driver 710, an elongated shaft 712 extending distally from the handle 711, and a driving bit 713 (FIG. 25) extending distally from the elongated shaft 712 and configured to engage and drive the set screw "S" into the pedicle screw housing 120 of the pedicle screw assembly 100.

The support sleeve 720 of the surgical system 700 defines a longitudinal axis "A4-A4." Although shown with a cylindrically shaped body, the support sleeve 720 may have any suitable shape and/or configuration. The support sleeve 720 includes an upper shaft portion 721 that extends to a distal surface 721b and has a first gripping portion 721a at proximal end, and which is configured for selective engagement with an anti-torque tool 730. The support sleeve 720 also defines a recessed portion 722 extending distally from the distal surface 721b of the upper shaft portion 721 and recessed therefrom. The support sleeve 720 further includes a tubular body 723 that extends distally from the recessed portion 722 and has a proximal end and a distal end. The proximal end of the tubular body 723 of the support sleeve 720 has a second gripping portion 723a configured for engagement with the anti-torque tool 730.

The first gripping portion 721a of the support sleeve 720 has a sidewall 721c defining one or more side surfaces 721d positioned to facilitate gripping and may be at the same or different angles relative to each other. Similarly, the second gripping portion 723a of the support sleeve 720 has a sidewall 723b defining one or more side surfaces 723c positioned to facilitate gripping and may be at the same or different angles relative to each other. In certain embodiments, one or both of the sidewalls 721c, 723b of the respective first and second gripping portions 721a, 723a of the support sleeve 720 may be textured, e.g., to facilitate gripping with anti-torque tool 730. In some embodiments, the sidewalls 721c, 723b of the respective first and second gripping portions 721a, 723a of the support sleeve 720 may define and suitable circular and/or non-circular profile configured for engagement with a torqueing instrument, e.g., the anti-torque tool 730, for example, such profile may include one or more configurations including hexagonal, star, square, circular, triangular, etc., and/or any combinations thereof.

In use, each of the first and second gripping portions 721a, 723a of the support sleeve 720 may be configured to receive one or more anti-torque tools 730, separately, and/or simultaneously, as desired. With the first gripping portion 721a positioned farther from the patient than the second gripping portion 723a, the first gripping portion 721a may provide additional leverage for manipulating the vertebrae (given the larger moment arm relative to the patient's vertebrae) as compared to the second gripping portion 723a.

The distal end of the tubular body 723 of the support sleeve 720 defines a first rod-engaging recess 724a (FIG. 23A) on a first side of the tubular body 723 and a second rod-engaging recess 724b (FIG. 24B) on a second side of the tubular body 723. The first and second rod-engaging recesses 724a, 724b are configured to engage the spinal rod "R" and may have an inverted U-shaped or arched configuration. The support sleeve 720 includes an inner surface 720a that defines a hollow passage 725 configured to selectively receive the pedicle screw assembly 100 and the driver 710 therein. The support sleeve 720 defines elongated channels 726a, 726b therealong. The elongated channels 726a, 726b may be configured to provide easy access to the inner surface 720a of support sleeve 720, e.g., for cleaning the inner surface 720a of the support sleeve 720. The elongated channels 726a, 726b may act as, e.g., as a window to provide a visual of the location of pedicle screw assembly 100 relative to the support sleeve 720. The support sleeve 720 may include indicia 727 (e.g., a laser marked line or the like) disposed on an outer surface of the tubular body 723 of the support sleeve 720. The indicia 727 can be used to determine the orientation of the pedicle screw assembly 100 relative to the support sleeve 720. For example, when the support sleeve 720 is fully seated onto the pedicle screw assembly 100, the top or proximal end of the head assembly 150 of the pedicle screw assembly 100 may align with the indicia 727 of the support sleeve 720.

Figure 26:
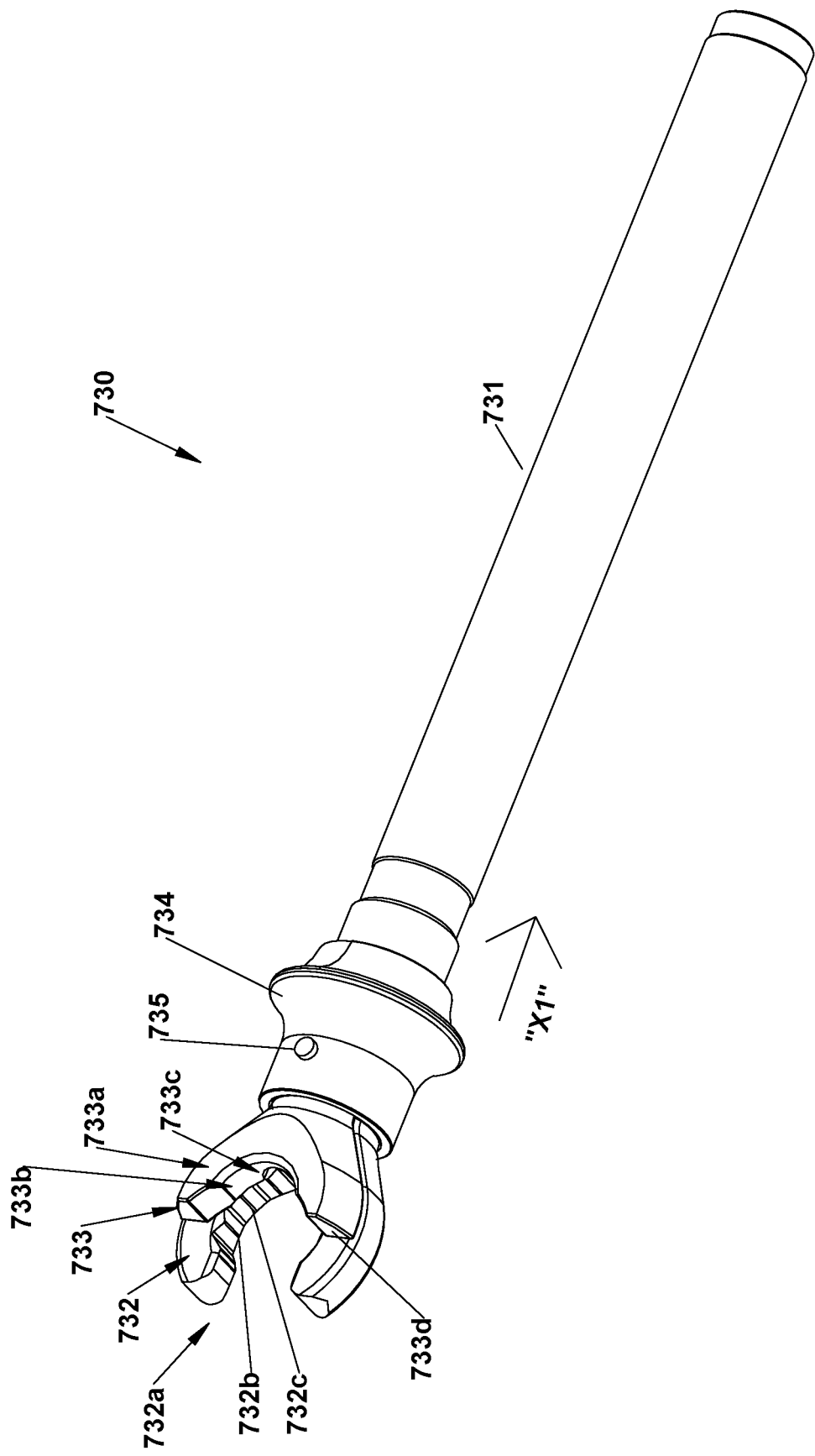
FIG. 26 is a perspective view of an anti-torque tool of the surgical system of FIG. 23A.

With reference to FIG. 26, the anti-torque tool 730 of the surgical system 700 includes an elongated shaft portion 731, a receiving member 732 configured to engage one of the first or second gripping portions 721a, 723a (FIG. 24A) of the support sleeve 720, a recess-receiving member 733 configured to engage the recessed portion 722 of the support sleeve 720, a knob 734 disposed along the elongated shaft portion 731 and configured to impart movement to the recess-receiving member 733, and a pin 735 that couples the recess-receiving member 733 to the knob 734.

The receiving member 732 of the anti-torque tool 730 has a first grasping portion 732b that defines an opening 732a. The first grasping portion 732b may include one or more grasping surfaces 732c with one or more teeth configured to engage or grip the first or second gripping portions 721a, 723a of the support sleeve 720 to inhibit the support sleeve 720 from rotating and/or to facilitate manipulation of the support sleeve 720 relative to the patient's vertebrae. The one or more grasping surfaces 732c of the first grasping portion 732b may be positioned at the same and/or different angles relative to one other. Similar to the first grasping portion 732b, the recess-receiving member 733 of the anti-torque tool 730 includes a second grasping portion 733c having one or more grasping surfaces 733d that define an opening 733b to enable the anti-torque tool 730 to grasp the recessed portion 722 of the support sleeve 720.

To operate the anti-torque tool 730, a force is applied to the knob 734 of the anti-torque tool 730 in an axial (e.g., proximally) direction "X1" so that the knob 734 slides axially along elongated shaft portion 731. By virtue of the recess-receiving member 733 being coupled to the knob 734 via the pin 735 of the anti-torque tool 730, the force applied in the axial direction "X1" causes a corresponding movement of the recess-receiving member 733 in the axial direction "X1" such that the recess-receiving member 733 is retracted, e.g., proximally, and misaligned with the receiving member 732. With the knob 734 coupled to a return spring (not shown) disposed within the elongated shaft portion 731 of the anti-torque tool 730, when the knob 734 is released, the return spring causes the knob 734 and the recess-receiving member 733 to return (e.g., distally) to an initial position in which the recess-receiving member 733 is aligned or substantially aligned with the receiving member 732, as seen in FIG. 26.

In use, the pedicle screw assembly 100 of the surgical system 700 can be installed into a vertebra, and the spinal rod "R" can be reduced into the pedicle screw housing 120 of the pedicle screw assembly 100. The support sleeve 720 of the surgical system 700 can be placed over, and advanced onto, the pedicle screw assembly 100 until the first and second rod-engaging recesses 724a, 724b of the support sleeve 720 engage the spinal rod "R." As desired, the anti-torque tool 730 can be placed onto the support sleeve 720.

To attach the anti-torque tool 730 to the support sleeve 720, for example, to one of the first or second gripping portions 721a, 723a of the support sleeve 720, the knob 734 of the anti-torque tool 730 can be pulled back in the axial direction "X1" by applying a force in the axial direction "X1," which causes the recess-receiving member 733 to be pulled back or retracted in the axial direction "X1." The receiving member 732 of the anti-torque tool 730 can be advanced toward the support sleeve 720 until the grasping portion 732b of the receiving member 732 of the anti-torque tool 730 surrounds a respective one of the first or second gripping portions 721a, 723a of the support sleeve 720. The anti-torque tool 730 can be moved down or distally onto the respective one of the first or second gripping portions 721a, 723a of the support sleeve 720 until the grasping portion 732b of the receiving member 732 of the anti-torque tool 730 engages with one of the first or second gripping portions 721a, 723a of the support sleeve 720.

With respect to the second gripping portion 723a of the support sleeve 720, in order to lock the anti-torque tool 730 onto the support sleeve 720, force applied to the knob 734 can be released, which causes recess-receiving member 733 to return (e.g., via the return spring, not shown) or snap back to the rest or initial position and engage the support sleeve 720. For example, with respect to the second gripping portion 723a of the support sleeve 720, as the recess-receiving member 733 returns, the recess-receiving member 733 becomes wedged between the receiving member 732 and the distal surface 721b of the upper shaft portion 721 of the support sleeve 720. Once the receiving member 733 is biased back to its initial position and secured to the support sleeve 720, the anti-torque tool 730 is locked onto the support sleeve 720 and is inhibited from premature removal from the support sleeve 720. The driver 710 of the surgical system 700 may be introduced into the pedicle screw assembly 100 and the support sleeve 720 to tighten the set screw "S" with the driving bit 713 of the driver 710. As the set screw "S" is tightened against the spinal rod "R," the spinal rod "R" is driven or seated into the pedicle screw housing 120 of the pedicle screw assembly 100. While tightening the set screw "S," a clinician may firmly grasp the elongated shaft portion 731 of the anti-torque tool 730 to inhibit the support sleeve 720 and/or the pedicle screw assembly 100 from rotating (e.g., rotationally fix) to facilitate driving and/or tightening of the set screw "S" so that the set screw "S" can secure the spinal rod "R" to the pedicle screw assembly 100. Once the set screw "S" is secured to the spinal rod "R," the driver 710 may be withdrawn proximally from the support sleeve 720.

To remove the anti-torque tool 730 from the support sleeve 720 with respect to either the first or second gripping portions 721a, 723a of the support sleeve 720, the anti-torque tool 730 can be moved up or proximally off, the first or second gripping portions 721a, 723a of the support sleeve 720 until the grasping portion 732b of the receiving member 732 of the anti-torque tool 730 is disengaged from the respective first or second gripping portions 721a, 723a of the support sleeve 720. The support sleeve 720 may then be moved proximally away from the pedicle screw assembly 100 to remove the support sleeve 720 from the pedicle screw assembly 100 and, e.g., out of a body cavity.

Alternatively, and or additionally, to remove the anti-torque tool 730 from the second gripping portion 723a of the support sleeve 720, force in the axial direction "X1" can be applied to the knob 734 of the anti-torque tool 730 to retract the recess-receiving member 733 and disengage the recess-receiving member 733 from the recessed portion 722. With the recess-receiving member 733 of the anti-torque tool 730 disengaged from the recessed portion 722 of the support sleeve 720, the recess-receiving member 733 is no longer wedged between the distal surface 721b of the upper shaft portion 721 of the support sleeve 720 and the receiving member 732 of the anti-torque tool 730 so that the anti-torque tool 730 can be separated from the support sleeve 720.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A system for spinal surgery, comprising:
a pedicle screw assembly including a screw securable to a spinal bone and a pedicle screw housing coupled to the screw, the pedicle screw housing defining a rod-receiving recess, the pedicle screw assembly including an extension assembly coupled to the pedicle screw housing by a frangible member;
a derotation sleeve mountable to the pedicle screw assembly, the derotation sleeve movable with the pedicle screw assembly to manipulate the spinal bone, the derotation sleeve configured to inhibit the frangible member from breaking while manipulating the spinal bone, wherein the derotation sleeve includes a lock positionable between a locked position and an unlocked position, such that the derotation sleeve is secured to the pedicle screw assembly when the lock is in the locked position, and the derotation sleeve is separable from the pedicle screw assembly when the lock is in the unlocked position, wherein the derotation sleeve includes an upper shaft portion and a lower shaft portion coupled to the upper shaft portion, the upper shaft portion being movable relative to the lower shaft portion to position the lock between the locked and unlocked positions; and a rod reducer mountable to the derotation sleeve and configured to reduce a spinal rod into the rod-receiving recess of the pedicle screw housing.

2. The system of claim 1, wherein the upper shaft portion of the derotation sleeve includes a sleeve assembly including an inner sleeve and an outer sleeve, the inner sleeve selectively attachable to the extension assembly of the pedicle screw assembly to secure the derotation sleeve to the pedicle screw assembly.

3. The system of claim 2, wherein the inner sleeve includes a finger and the extension assembly defines a groove configured to selectively receive the finger.

4. The system of claim 2, wherein the derotation sleeve includes a knob rotatable relative to the inner sleeve to move the outer sleeve axially relative to the inner sleeve until the outer sleeve engages the lower shaft portion to restrain movement of the upper shaft portion relative to the lower shaft portion when the lock is positioned in the locked position.

5. The system of claim 1, wherein the rod reducer includes a cap that is threadably engagable with a proximal end of the derotation sleeve to couple the rod reducer to the derotation sleeve.

6. The system of claim 5, wherein the cap of the rod reducer is coupled to a sleeve assembly of the rod reducer, the sleeve assembly of the rod reducer includes an outer sleeve and an inner sleeve, the outer sleeve of the rod reducer is rotatable relative to the cap and the inner sleeve of the rod reducer to axially advance the inner sleeve of the rod reducer along the pedicle screw assembly and reduce the spinal rod into the rod-receiving recess of the pedicle screw housing of the pedicle screw assembly.

7. A system for spinal surgery, comprising:
a pedicle screw assembly including a screw securable to a spinal bone and a pedicle screw housing coupled to the screw, the pedicle screw housing defining a rod-receiving recess, the pedicle screw assembly including an extension assembly coupled to the pedicle screw housing and extending proximally therefrom;
a derotation sleeve mountable to the pedicle screw assembly, the derotation sleeve having a locking member for securely engaging a locking feature of the extension assembly to prevent separation of the derotation sleeve from the pedicle screw assembly;
wherein a proximal portion of the derotation sleeve is rotatable about a longitudinal axis of the derotation sleeve with respect to a distal portion of the derotation sleeve to move the locking member out of engagement with the locking feature, and wherein the proximal portion of the derotation sleeve is lockable to prevent rotation of the proximal portion with respect to the distal portion, the proximal portion of the derotation sleeve being lockable by rotating a knob of the derotation sleeve about the longitudinal axis.

8. The system of claim 7, wherein the locking feature is a groove elongated in a direction transverse to a longitudinal dimension of the extension assembly.

9. The system of claim 8, wherein the locking member is a finger configured to selectively engage the groove.

10. The system of claim 9, wherein the finger is deflectable to snap into the groove.

11. The system of claim 10, wherein rotation of the proximal portion of the derotation sleeve about the longitudinal axis causes the finger to cam out of the groove.

12. The system of claim 7, wherein the proximal portion of the derotation sleeve is lockable by advancing the proximal portion distally towards the distal portion.

13. The system of claim 12, wherein advancing the proximal portion of the derotation sleeve distally towards the distal portion includes causing teeth to engage corresponding recesses at an interface between the proximal portion and the distal portion of the derotation sleeve.

14. The system of claim 7, wherein the extension assembly of the pedicle screw assembly includes a pair of longitudinal extensions, each of the longitudinal extensions extending proximally from a respective distal end coupled to the pedicle screw housing, and wherein the derotation sleeve includes a first leg and a second leg spaced apart from one another and elongated along a longitudinal direction parallel to the longitudinal axis, each of the first and second legs being configured to be positioned alongside a respective one of the pair of longitudinal extensions when the derotation sleeve is mounted to the pedicle screw assembly.

15. The system of claim 14, wherein each of the longitudinal extensions of the pedicle screw assembly is coupled to the pedicle screw housing by a respective frangible member, and wherein each of the first and second legs is configured to extend adjacent to a respective one of the frangible members when the derotation sleeve is mounted to the pedicle screw assembly.

16. The system of claim 7, further including a rod reducer securable over the derotation sleeve and configured to reduce a spinal rod into the rod-receiving recess of the pedicle screw.

17. The system of claim 16, wherein the rod reducer has a proximal portion securable to a proximal end of the derotation sleeve, the rod reducer including a sleeve portion extending distally from the proximal portion, the sleeve portion being advanceable distally along the longitudinal axis to push the spinal rod distally when the rod reducer is secured to the derotation sleeve.

* * * * *